US00RE36187E

United States Patent [19]

Townsend et al.

[11] E Patent Number: Re. 36,187

[45] Reissued Date of Patent: Apr. 6, 1999

[54] ACYCLIC PYRROLO [2,3-D]PYRIMIDINE ANALOGS AS ANTIVIRAL AGENTS

[75] Inventors: Leroy B. Townsend; John G. Drach, both of Ann Arbor; Charles Shipman, Jr., Dexter; Jeffrey S. Pudlo, Ann Arbor, all of Mich.

[73] Assignee: The Regents of the University of Michigan, Ann Arbor, Mich.

[21] Appl. No.: 287,290

[22] Filed: Aug. 5, 1994

Related U.S. Patent Documents

Reissue of:

[64] Patent No.: 4,968,686
Issued: Nov. 6, 1990
Appl. No.: 369,262
Filed: Jun. 21, 1989

U.S. Applications:

[63] Continuation-in-part of Ser. No. 179,081, Apr. 8, 1988, Pat. No. 4,927,830.

[51] Int. Cl.[6] ..... A61K 31/505; C07D 487/06

[52] U.S. Cl. ..... 514/258; 544/280; 544/232; 544/244

[58] Field of Search ..... 544/280, 244, 544/232; 514/258

[56] References Cited

U.S. PATENT DOCUMENTS

| | | | |
|---|---|---|---|
| 3,037,980 | 6/1962 | Hitchings et al. | 544/280 |
| 3,311,628 | 3/1967 | Partyka | 544/280 |
| 3,631,036 | 12/1971 | Kim et al. | 544/280 |
| 3,817,982 | 6/1974 | Verheyden et al. | 544/280 |
| 3,867,386 | 2/1975 | Kim et al. | 544/280 |
| 3,962,211 | 6/1976 | Townsend et al. | 544/262 |
| 4,199,574 | 4/1980 | Schaeffer | 544/244 |
| 4,229,453 | 10/1980 | Roth et al. | 544/280 |
| 4,596,798 | 6/1986 | Shipman, Jr. et al. | 514/183 |
| 4,927,830 | 5/1990 | Townsend et al. | 514/258 |

FOREIGN PATENT DOCUMENTS

| | | |
|---|---|---|
| 3036390 | 5/1982 | Germany . |
| 3145287 | 5/1983 | Germany . |
| 03142 | 5/1988 | WIPO . |

OTHER PUBLICATIONS

Vindelov, L.L., "Flow Microfluorometric Analysis of Nuclear DNA in Cells from Solid Tumors and Cells Suspensions," *Vichows Arch. B Cell Path.* 24:277–242 (1977).

Sigma Chemical Co. Catalog, St. Louis, MO., 1984, p. 898.

Robins, M.J. et al., "A Mild Conversion of Vicinal Diols to Alkenes. Efficient Transformation of Ribonucleosides into 2'–Ene and 2',3'–Dideoxynucleosides," *Tetrahedron Letters* 25:367–370 (1984).

Saxena, N.K. et al., "Synthesis and Antiviral Activity of Certain 4–Substituted and 2,4–Disubstituted 7–[(2–Hydroxyethoxy)methyl]pyrrolo[2,3–d]pyrimidines," *J. Med. Chem.* 31:1507–1506 (1988).

Shipman, Jr., C., "Evaluation of 4–(2–Hydroxyethyl)–1–Piperazineethanesulfonic Acid (HEPES) as a Tissue Culture Buffer," *Proc. Sci. Exp. Biol. Med.* 120:305–310 (1969).

Shipman, Jr. C. et al., "Antiviral Activity of Arabinosyladenine and Arabinosylhypoxanthine in Herpes Simplex Virus–Infected KB Cells: Selective Inhibition of Viral Deoxyribonucleic Acid Synthesis in Synchronized Suspension Cultures," *Antimicro. Agents Chemother.* 9:120–127 (1976).

Smith, C.M. et al., "Inhibitors of Hypoxanthine Metabolism in Ehrlich Ascites Tumor Cells in Vitro," *Can. Treat. Rpts.* 60:1567–1584 (1976).

Tolman, R.L. et al., "Pyrrolopyrimidine Nucleosides. III. The Total Synthesis of Toyocamycin, Sangivamycin, Tubercidin, and Related Derivatives," *J. Am. Chem. Soc.* 91:2102–2108 (1969).

Turk, S.R. et al., "Pyrrolo[2,3–d]Pyrimidine Nucleosides as Inhibitors of Human cytomegalovirus," *Antimicro. Agents Chemother.* 31:544–550 (1987).

Mitsuya, H. et al., "3'–Azido–3'–deoxythymidine (BW A509U): An Antiviral Agent that Inhibits the Infectivity and Cytopathic Effect of Human T–Lymphotropic Virus Type III/Lymphadenopathy–Associated Virus in Vitro," *PNAS (USA)* 82:7096–7100 (1985).

Mitsuya, H. et al., "Inhibition of the in Vitro Infectivity and Cytopathic Effect of Human T–Lymphotrophic Virus Type III/Lymphadenopathy–Associated Virus (HTLV–III/LAV) by 2',3'–Dideoxynucleosides," *PNAS (USA)* 83:1911–1915 (1986).

Nassiri, M.R., "3rd Annual Meeting Clinical Applications of Cytometry," Sep. 1988 (Abstract).

Pudlo, J.S. et al., "Synthesis and Antiviral Activity of Certain 4– and 4,5–Disubstituted 7–[(2–Hydroxyethoxy)Methyl]Pyrrolo[2,3–$^d$]Pyrimidines," *J. Med. Chem.* 31:2086–2092 (1988).

Ramasamy, K. et al., "Total Synthesis of 2'–Depxutpupca, ucom. 2'–Deoxysangivamycin and Related 7–β–D–Arabinofuranosyl–Pyrrolo[2,3–d]Pyrimidines via Ring Closure of Pyrrole Precursors Prepared by the Sterospecific Sodium Salt Glycosylation Procedure," Abstract 65, Tetrahedron, 42(21), (1986), pp. 5869–5878.

Robins, M.J. et al., "Nucleic Acid Related Compounds. 24 Transformation of Tubercidin 2',3'–O–Orthoacetate into Halo, Deoxy, Epoxide, and Unsaturated Sugar Nucleosides," *Can. J. Chem.* 55:1251–1259 (1977).

Drach, J.C., "28 ICAAC, Los Angeles, Calif." Oct. 1988 (Abstract).

(List continued on next page.)

*Primary Examiner*—John M. Ford
*Attorney, Agent, or Firm*—Harness, Dickey & Pierce, P.L.C.

[57] ABSTRACT

This invention relates to the use of acyclic substituted pyrrolo[2,3-d]pyrimidine nucleoside analogs in the treatment of viral infections. Such substituted compounds retain antiviral properties present in their parent compounds, yet exhibit significantly decreased levels of cytotoxicity, thereby having therapeutic potential as antiviral agents.

15 Claims, 3 Drawing Sheets

OTHER PUBLICATIONS

Figure 1:
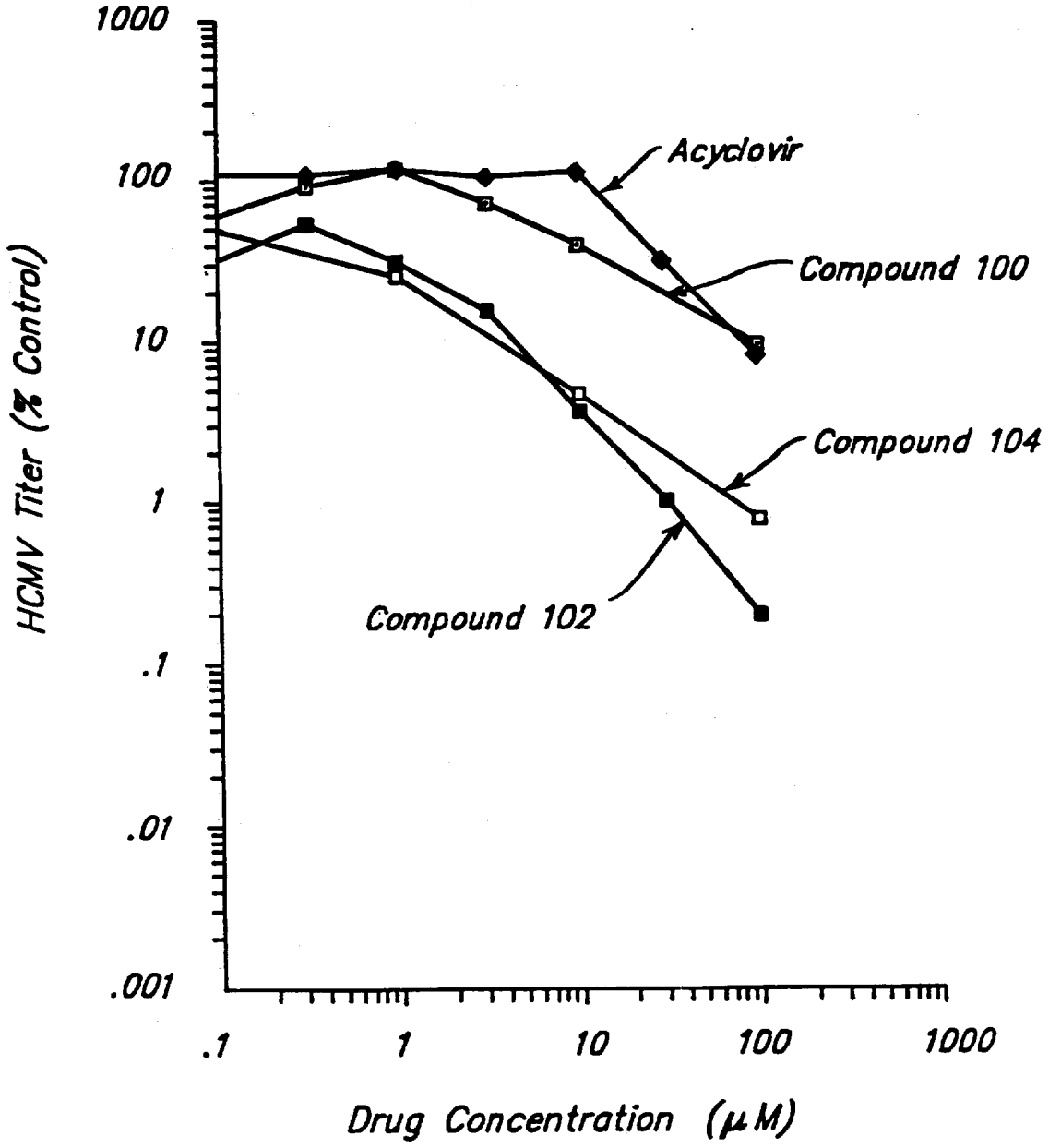

Duffy, T.D. et al., "Pyrrolo[2,3–d]Pyrimidines. Synthesis from 4–Pyrimidylhydrazones, a 2–Bis(Methylthio)Methyleneaminopyrrole–3–Carbonitrile, and a Pyrrolo–[2,3–d][1, 3]Thiazine–2(1H)–Thione," *J. Chem. Soc. Perkin Trans.* 16:1921–1929 (1974).

Gadler, H., "Nucleic Acid Hybridization for Measurement of Effects of Antiviral Compounds on Human Cytomegalovirus DNA Replication," *Antimicro. Agents Chem.* 24:370–374 (1983).

Gupta, P.K. et al., "Synthesis, Cytotoxicity, and Antiviral Activity of Some Acyclic Analogues of the Pyrrolo[2,3–d] Pyrimidine Nucleoside Antibiotics Tubercidin, Toyocamycin, and Sangivamycin," *J. Med. Chem.* 32:402–408 (1989).

Hansske, F. et al., "2' and 3'–Ketonucleosides and Their Arabino and Xylo Reduction Products," *Tetrahedron* 40:125–135 (1984).

Jain, T.C. et al., "Reactions of 2–Acyloxyisobutyrl Halides with Nucleosides. II. Reactions of Tubercidin and Formycin," *J. Org. Chem.* 33:3179–3186 (1973).

Maruyama T. et al., "Pyrrolopyrimidine Nucleosides. 18.[1] Synthesis and Chemotherapeutic Activity of 4–Amino–7–(3–deoxy–β–D–ribofuranosyl)pyrrolo[2,3–d]pyrimidine–5–carboxamide—(3'–Deoxysangivamycin) and 4–Amino–7–(2–deoxy–β–D–ribofuranosyl)pyrrolo[2,3–d]pyrimidine 5–carboxamide (2'–Deoxysangivamycin)," *J. Med. Chem* 26:25–29 (1983).

Bergstrom, D.E. et al., "Antiviral Activity of C–5 Substituted Tubercidin Analogues," *J. Med. Chem.* 27:285–292 (1984).

De Clercq, E. et al., "Nucleic Acid Related Compounds. 51. Synthesis and Biological Properties of Sugar–Modified Analogues of the Nucleoside Antibiotics Tubercidin, Toyocamycin, Sangivamycin, and Formycin," *J. Med. Chem.* 30:481–486 (1987).

De Clercq, E. et al., "Antirhinovirus Activity of Purine Nucleoside Analogs," *Antimicro. Agents Chemother.* 29:482–487 (1986).

Drach, J.C. et al., "Tritiated Thymidine Incorporation Does Not Measure DNA Synthesis in Ribavirin–Treated Human Cells," *Science* 212:549–551 (1981).

ACYCLIC PYRROLO [2,3-D]PYRIMIDINE ANALOGS AS ANTIVIRAL AGENTS

Matter enclosed in heavy brackets [ ] appears in the original patent but forms no part of this reissue specification; matter printed in italics indicates the additions made by reissue.

CROSS-REFERENCE TO RELATED APPLICATION

This is a continuation-in-part of U.S. patent application Ser. No. 179,081 filed Apr. 8, 1988, *now U.S. Pat. No. 4,927,830,* entitled "Acyclic Pyrrolo[2,3-d]Pyrimidine Analogs As Antiviral Agents".

This invention was made with Government support under contracts numbered NO1AI142554 and NO1AI72641 awarded by the National Institute of Allergy and Infectious Diseases. The Government has certain rights in this invention.

I. BACKGROUND OF THE INVENTION

The present invention relates to the use of certain deazapurine nucleoside analogs in the treatment of viral infections. More particularly, the present invention relates to the use of certain pyrrolo[2,3-d]pyrimidine nucleoside analogs against human cytomegalovirus and herpes simplex virus type 1.

Broad spectrum antiviral activity of pyrrolo[2,3-d] pyrimidine nucleosides such as tubercidin, sangivamycin and toyocamycin and some substituted derivatives has been previously reported. Activity of those compounds against specific viruses, such as RNA rhinovirus and DNA herpes simplex virus type 1 and type 2 has also been reported. See, for example, Bergstrom, D. E. et al., J. Med. Chem., 27: 285–292 (1984); and DeClercq, E. et al., Antimicrob. Agents Chemother., 29:482–487 (1986).

Pyrrolo[2,3-]pyrimidine nucleosides are particularly attractive as potential antiviral agents because of their stability toward the two major pathways of bioactive purine nucleoside inactivation, deamination by adenosine deaminase and glycosidic bond cleavage by purine nucleoside phosphorylases. Unfortunately, pyrrolo[2,3-d]pyrimidine nucleosides which have been previously described as potently antiviral also exhibit unacceptable levels of cytotoxicity, thereby diminishing their usefulness in treatment of viral infections in animals.

It would thus be very desirable to discover derivatives of these compounds having decreased cytotoxicity while retaining their antiviral properties. Such a discovery has been made and is the basis for the present invention which relates to a class of 4, 5, 6, 7-substituted pyrrolo[2,3-d] pyrimidine analogs which exhibit levels of cytotoxicity significantly lower than their parent compounds, yet retain antiviral activity, particularly against DNA human cytomegalovirus (HCMV) and herpes simplex virus type 1 (HSV-1).

II. SUMMARY OF THE INVENTION

The present invention relates to the treatment of viral infections, and, more particularly, human cytomegalovirus (HCMV) and herpes simplex virus type 1 (HSV-1) infections, with a therapeutically-effective amount of a compound selected from a group consisting of compounds of the following formula and pharmaceutically acceptable salts thereof:

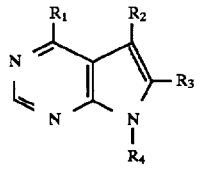

where $R_1$ is $NH_2$, NHOH, OH or H;

$R_2$ is $CSNH_2$, Cl, Br, I, F, 2-buten-1-yl, 5-(1-hydroxyethyl) or 5-(1-methoxyethyl);

$R_3$ is H, $NH_2$ or Br; and $R_4$ is (1,3-dihydroxy-2-propoxy)methyl, (2-hydroxyethoxy)methyl; (2-acetoxyethoxy)methyl, 2-hydroxy-1-(1,3-dihydroxy-2-propoxy)ethyl, (2-phosphonylmethoxy)ethyl or 3-hydroxy-2-phosphonylmethoxypropyl.

III. BRIEF DESCRIPTION OF THE DRAWINGS

Figure 2:
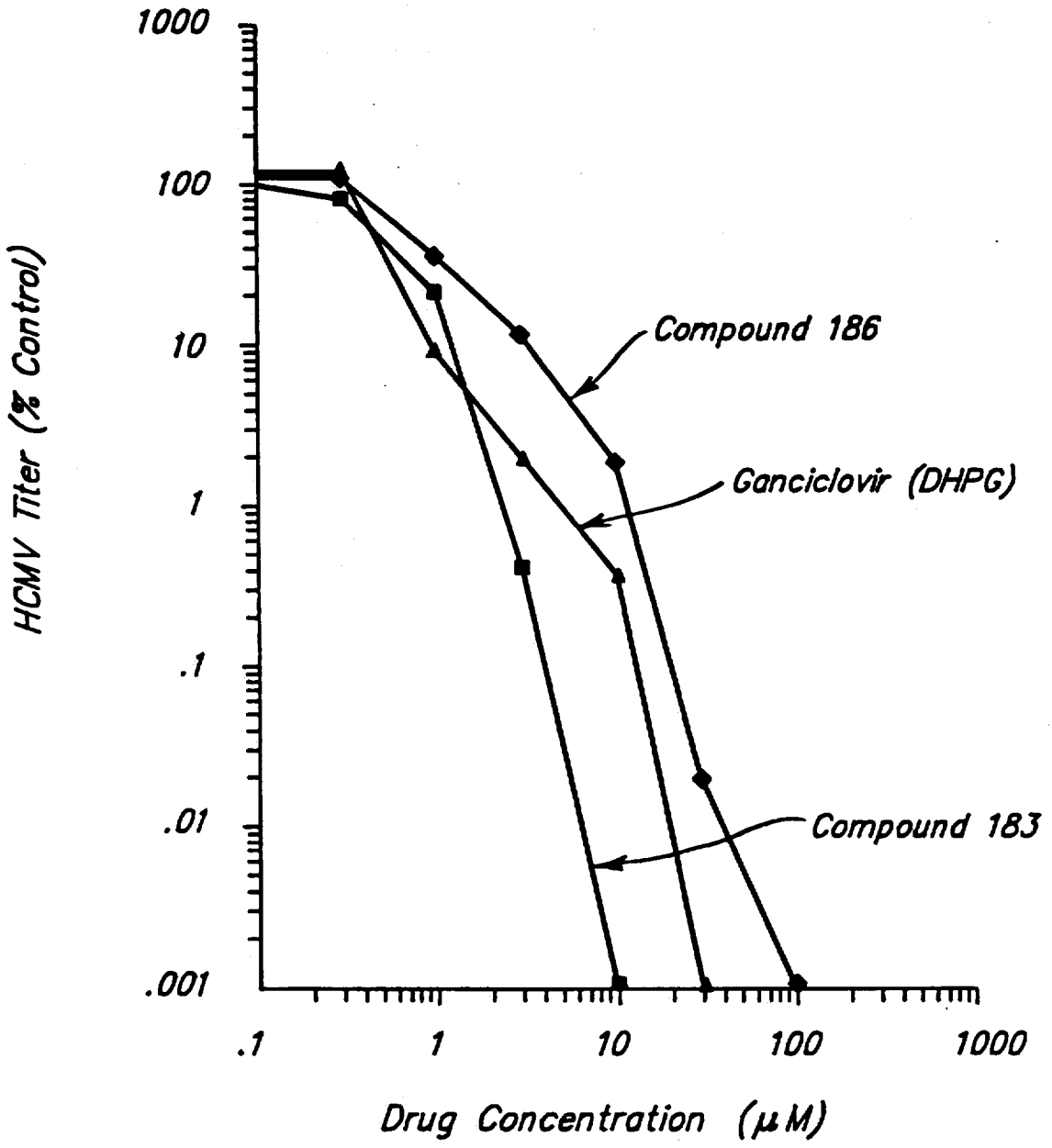
Figure 3:
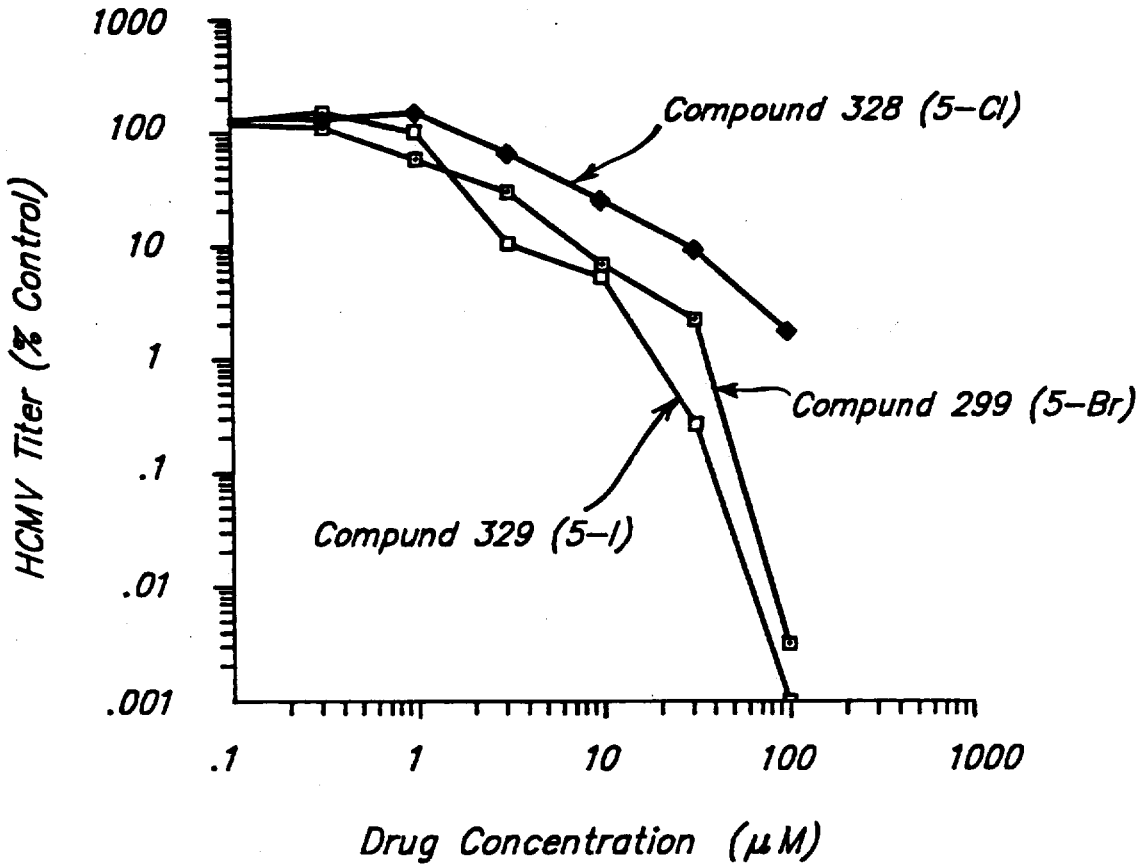

FIGS. 1, 2 and 3 are graphs showing HCMV titer reduction by antiviral compounds in accordance with the present invention.

IV. DETAILED DESCRIPTION OF THE PREFERRED EMBODIMENTS OF THE INVENTION

A. CHEMICAL STRUCTURE OF COMPOUNDS

The present invention relates to the treatment of viral infections with pyrrolo[2,3-d]pyrimidine analogs of the following formula and pharmaceutically acceptable salts thereof:

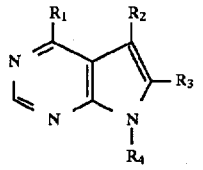

where $R_1$ is $NH_2$, NHOH, OH or H;

$R_2$ is $CSNH_2$, Cl, Br, I, F, 2-buten-1-yl, 5-(1-hydroxyethyl) or 5(-1-methoxyethyl);

$R_3$ is H, $NH_2$ or Br; and $R_4$ is (1,3-dihydroxy-2-propoxy)methyl, (2-hydroxyethoxy)methyl, (2-acetoxyethoxy)methyl, 2-hydroxy-1-(1,3-dihydroxy-2-propoxy)ethyl, (2-phosphonylmethoxy)ethyl or 3-hydroxy-2-phosphonylmethoxypropyl.

Specific compounds of the present invention include the following preferred compounds:

1. 4-amino-5-chloro-7-(2-hydroxyethoxymethyl)pyrrolo [2,3-d]pyrimidine, where $R_1$ is $NH_2$, $R_2$ is Cl, $R_3$ is H and $R_4$ is —$CH_2$—$OCH_2$—$CH_2OH$;
2. 4-amino-5-bromo-7-(2-hydroxyethoxymethyl)pyrrolo-[2,3-d]pyrimidine, where $R_1$ is $NH_2$, $R_2$ is Br, $R_3$ is H and $R_4$ is —$CH_2$—$OCH_2$—$CH_2OH$;
3. 4-amino-5-iodo-7-(2-hydroxyethoxymethyl)pyrrolo-[2,3-d]pyrimidine, where $R_1$ is $NH_2$, $R_2$ is I, $R_3$ is H and $R_4$ is —$CH_2$—$OCH_2$—$CH_2OH$;

4. 4-amino-5-chloro-7-[(1,3-dihydroxy-2-propoxy) methyl]pyrrolo[2,3-d]pyrimidine, where $R_1$ is $NH_2$, $R_2$ is Cl, $R_3$ is H and $R_4$ is —$CH_2$—O—$CH(CH_2OH)_2$;
5. 4-amino-5-bromo-7-[(1,3-dihydroxy-2-propoxy) methyl]-pyrrolo[2,3-d]pyrimidine, where $R_1$ is $NH_2$, $R_2$ is Br, $R_3$ is H and $R_4$ is —$CH_2$—O—$CH(CH_2OH)_2$;
6. 4amino-5-iodo-7-[(1,3-dihydroxy-2-propoxy)methyl]-pyrrolo[2,3-d]pyrimidine, where $R_1$ is $NH_2$, $R_2$ is I, $R_3$ is H and $R_4$ is —$CH_2$—O—$CH(CH_2OH)_2$;
7. 4-amino-5-thiocarboxamide-7-[(1,3-dihydroxy-2-propoxy)methyl]pyrrolo[2,3-d]pyrimidine, where $R_1$ is $NH_2$, $R_2$ is $CSNH_2$, $R_3$is H and $R_4$ is —$CH_2$—O—$CH(CH_2OH)_2$;
8. 4-amino-5-thiocarboxamide-7-(2-hydroxyethoxymethyl)-pyrrolo[2,3-d]pyrimidine, where $R_1$ is $NH_2$, $R_2$ is $CSNH_2$, $R_3$ is H and $R_4$ is —$CH_2$—$OCH_2$—$CH_2OH$;
9. 4-hydroxy-5-chloro-7-[(1,3-dihydroxy-2-propoxy) methyl]pyrrolo[2,3-d]pyrimidine, where $R_1$ is OH, $R_2$ is Cl, $R_3$ is H and $R_4$ is —$CH_2$—O—$CH(CH_2OH)_2$;
10. 4-hydroxylamino-5-chloro-7-[(1,3-dihydroxy-2-propoxy)methyl]pyrrolo[2,3-d]pyrimidine, where $R_1$ is NHOH, $R_2$ is Cl, $R_3$ is H and $R_4$ is —$CH_2$—O—$CH(CH_2OH)_2$;
11. 4-hydroxy-5-bromo-7-[(1,3-dihydroxy-2-propoxy)-methyl]pyrrolo[2,3-d]pyrimidine, where $R_1$ is OH, $R_2$ is Br, $R_3$ is H and $R_4$ is —$CH_2$—O—$CH(CH_2OH)_2$;
12. 4-hydroxylamino-5-bromo-7-[(1,3-dihydroxy-2-propoxy)methyl]pyrrolo[2,3-d]pyrimidine, where $R_1$ is NHOH, $R_2$is Br, $R_3$ is H and $R_4$ is —$CH_2$—O—$CH(CH_2OH)_2$; and
13. 4-hydroxylamino-5-iodo-7-[(1,3-dihydroxy-2-propoxy)methyl]pyrrolo[2,3-d]pyrimidine, where $R_1$ is NHOH, $R_2$ is I, $R_3$ is H and $R_4$ is —$CH_2$—O—CH—$(CH_2OH)_2$.

B. METHOD OF USE OF COMPOUNDS

The compounds of the present invention exhibit anti-viral activity and acceptable cytotoxicity for use as therapeutic agents. In particular, it has been found that these compounds are effective against HCMV and HSV-1. The compounds are thus useful in the treatment of viral infections caused by HCMV and HSV-1 as well as other viruses. A partial list of viruses contemplated to be treatable with the compounds of the present invention includes: herpes simplex virus types 1 and 2; human cytomegalovirus; human immunodeficiency virus; human herpesvirus 6; varicella-zoster virus; Epstein-Barr virus; herpesvirus simiae; equine herpesvirus-1, 2 and 3; neurolymphomatosis (Marek's disease); influenza viruses A, B and C; parainfluenza viruses-1, 2, 3 and 4; adenovirus reovirus; respiratory syncytial virus; rhinovirus; coxsackie virus; echo virus; rubeola virus; hepatitis viruses; and papovavirus.

A compound of the present invention can be used in the treatment of viral infections in animals in accordance with conventional procedures, such as an active ingredient in pharmaceutical compositions, which can be administered orally, parenterally, topically, transdermally or by inhalation. The pharmaceutical compositions may take the form of tablets, lozenges, granules, capsules, pills, ampoules, (i.e. using suppositories or adhesive patches). They may also take the form of ointments, gels, pastes, creams, sprays, lotions, suspensions, solutions and emulsions of the active ingredient in aqueous or nonaqueous diluents, syrups, granulates or powders. In addition to a compound of the present invention, the pharmaceutical compositions can also contain other pharmaceutically active compounds or a plurality of compounds of the present invention.

C. METHOD OF SYNTHESIS

1. General Synthesis Schemes

The compounds of the present invention can be synthesized in accordance with the procedures described below. As shown in the following general synthesis schemes, the appropriate pyrrolo[2,3-d]pyrimidine analog can be condensed with an appropriate precursor for the ultimate R groups. This furnishes substituted pyrrolo[2,3-d]pyrimidines which are amenable toward subsequent chemical transformations to afford the requisite compounds. The solvent, reagents and reaction conditions for the preparation of some representative intermediate and target compounds are presented in detail hereinafter.

Scheme 1

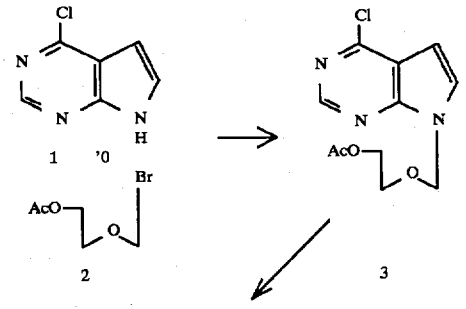

-continued
Scheme 1
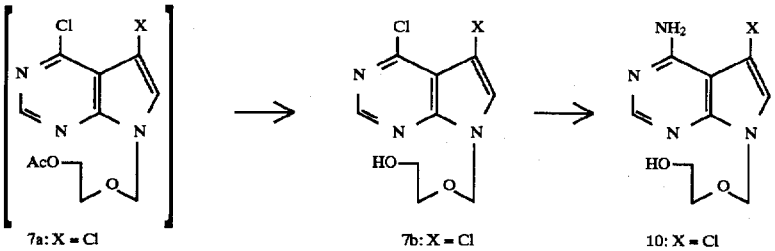
7a: X = Cl
8a: X = Br
9a: X = I
7b: X = Cl
8b: X = Br
9b: X = I
10: X = Cl
11: X = Br
12: X = I
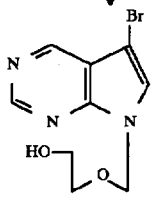
13a: R = OH
13b: R = NHOH
Scheme 2
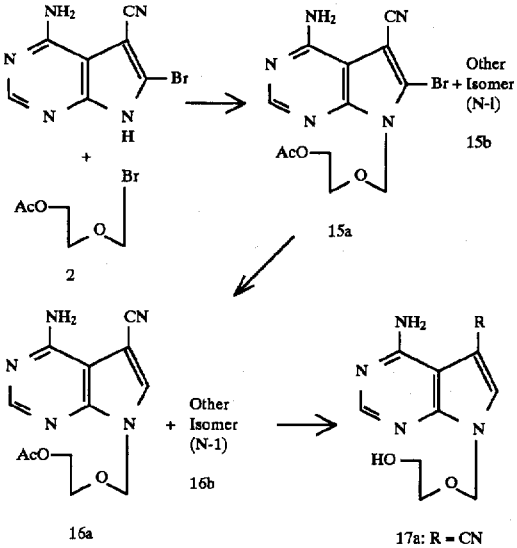
15a
Other Isomer (N-1) 15b
16a
Other Isomer (N-1) 16b
17a: R = CN
17c: R = $CSNH_2$
-continued
Scheme 2
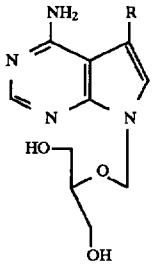
18a: R = CN
18c: R = $CSNH_2$
Scheme 3
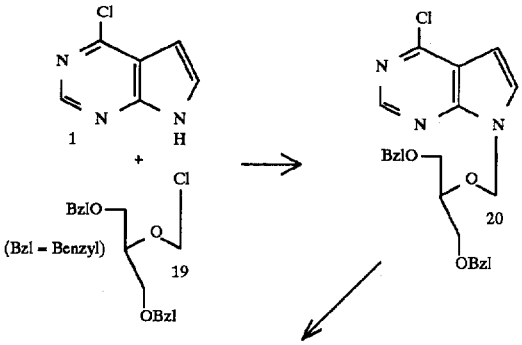
(Bzl = Benzyl)
19
20

-continued

Scheme 3

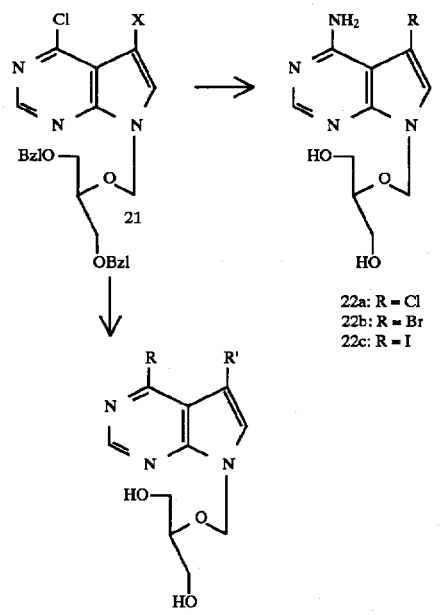

2. Specific Examples of chemical Synthesis

The compound numbering in this section refers to the numerals in the above reaction schemes.

a.

4-Chloro-7-(2-acetoxyethoxymethyl)pyrrolo[2,3-d] pyrimidine (3)

Sodium hydride (0.09 g, 60% in mineral oil) was added to a solution of 4-chloropyrrolo[2,3-d]pyrimidine (1) in dry DMF (6 mL) in small portions at 0°–5° C. under a nitrogen atmosphere. When all hydrogen evolution ceased, 2-acetoxyethoxymethyl bromide (2) (0.45 g) was added, dropwise with stirring, at room temperature. The reaction mixture was then stirred at room temperature for an additional 3 hours. After that period of time, 50 mL water was added and the product was extracted with ethylacetate. The ethylacetate layer was separated, washed with cold water, dried over anhydrous $Na_2SO_4$ and the solvent then evaporated under reduced pressure and temperature to afford a thick syrup. This syrup was applied to the top of a silica gel column (20×2 cm) and the column was eluted with 1% MeOH in $CHCl_3$.

All the fractions containing UV absorbing material were combined and the solvent from these fractions was evaporated to yield a colorless syrup which was crystallized from methanol as colorless needles to yield 0.21 g of 3 (40.2%), mp 87°–88° C. $^1$H-NMR (DMSO-$d_6$): δ8.5 (s, 1, C2-H), 7.88 (d, 1, J=3.5 Hz, C6-H), 6.72 (d, 1, J=3.6 Hz, C5-H), 5.7 (s, 2, N7-$CH_2$), 4.03 (m, 2, $OCH_2$), 3.52 (m, 2, $CH_2$), 1.92 (s, 3, OAc): UV$\lambda_{max}$nm (ε×10$^4$): (pH 7) 223 (1.2), 276 (2.4); (pH 1) 225 (1.2), 274 (0.25); (pH 11) 227 (0.8), 276 (0.2). Anal. Calcd. for $C_{11}H_{12}N_3O_3Cl$.0.5 MeOH: C,50.43; H, 5.6; N, 14.711. Found: C,50.91; H. 5.08; N, 14.43.

b.

4,5-Dichloro-7-(2-hydroxyethoxymethyl)pyrrolo[2, 3-d]pyrimidine (7b)

N-Chlorosuccinimide was added to a solution of 4-chloro-7-(2-acetoxyethoxymethyl)pyrrolo[2,3-d]pyrimidine (3) (0.35 g) in dry methylene chloride (15 mL). The reaction mixture was stirred at room temperature for 8 days. At that time, TLC established a complete disappearance of starting material. Water (50 mL) was added to the mixture and the product was extracted with $CHCl_3$ (3×30 mL). The chloroform extracts were combined and washed with water, then dried over anhydrous $Na_2SO_4$. The solvent was removed at 40° C. in vacuo and the resulting thick syrup was subjected to column chromatography. Elution of the silica gel column (15×2 cm) with benzene; chloroform (1:1), yielded a colorless oil (single spot on TLC) after evaporation of all the UV absorbing fractions at a reduced temperature and pressure, which was crystallized from ethyl alcohol to afford colorless needles of the acetylated intermediate, (7a, 0.23 g) (59.95%). 4,5-Dichloro-7-(2-acetoxyethoxymethyl)pyrrolo [2,3-d]pyrimidine (7a, 0.31 g) was then dissolved in dry methanol (15 mL) and to this solution was added methanol which had previously been saturated with ammonia at 0° C. (25 mL). The reaction mixture was stirred in a pressure bottle at room temperature for 20 hours. The solvent was evaporated at 30° C. in vacuo and the semi-solid mass was subjected to column chromatography. Elution of the product from a silica gel column (15×2 cm) with 2% MeOH in $CHCl_3$ yielded a colorless compound, after evaporation of all the appropriate UV absorbing fractions.

This solid was recrystallized from MeOH to furnish 0.11 g of 7 (40.74%), mp 142°–143° C. $^1$H-NMR (DMSO-$d_6$): δ8.74 (s, 1, C2-H), 8.13 (s, 1, C6-H), 5.66 (s, 2, $N_7$-$CH_2$), 4.65 (t, 1, J=5.3 Hz, exchangeable with $D_2O$, OH), 3.42 (m, 4, $CH_2$): UV$\lambda_{max}$nm (ε×10$^4$): (pH 7) 230 (3.3), 271 (0.6), 292 (0.6); (pH 1) 230 (2.8), 292 (0.6); (pH 11) 236 (2.8), 271 (0.4), 294 (0.4). Anal. Calcd. for $C_9H_9N_3O_2Cl_2$: C, 41.22, H, 3.43; N, 16.03. Found: C, 41.29; H, 3.65; N, 15.85.

c.

4-Chloro-5-bromo-7-(2-hydroxyethoxymethyl) pyrrolo[2,3-d]-pyrimidine (8b)

A mixture of 4-chloro-7-(2-acetoxyethoxymethyl)pyrrolo [2,3-d]pyrimidine (3, 0.2 g) and N-bromosuccinimide (0.10 g) was dissolved in dry methylene chloride (10 mL). The reaction mixture was stirred at room temperature for 20 hours. The solvent was evaporated at 40° C. under reduced pressure to give a semi-solid mass which was recrystallized from MeOH as a light brown solid (8a 0.11 g, 50%).

The solid (8a, 0.3 g) was dissolved in dry methanol (10 mL) and to this solution was added methanol saturated with ammonia (20 mL). The reaction mixture was stirred, in a pressure bottle, at room temperature for 20 hours. The solvent was removed at 70° C. under reduced pressure in vacuo and the semi-solid mass was purified by column chromatography. Elution of the silica gel column (15×2 cm) with 2% MeOH in $CHCl_3$ yielded a colorless syrup after evaporation of the appropriate UV absorbing fractions.

Trituration of this syrup with ether gave a colorless compound, which was recrystallized from $CHCl_3$ to give 0.11 g of 8b (38.02%), mp 135°–136° C. $^1$H-NMR (DMSO-$d_6$): δ8.72 (s, 1, C2-H), 8.15 (s, 1, C6—H), 5.66 (s, 2, N7—$CH_2$), 4.63 (t, 1, exchangeable with $D_2O$, OH), 3.46 (m, 4, $CH_2$): UV $\lambda_{max}$nm (ε×10$^4$): (pH 7) 230 (2.5), 270

(0.3), 298 (0.35); (pH 1) 231 (2.7), 270 (0.3); (pH 11) 232 (2.6), 370 (0.3), 301 (0.35). Anal. Calcd. for $C_9H_9N_3O_2BrCl$: C, 35.24; H, 2.93; N, 13.70. Found: C, 34.77; H, 3.21; N, 13.48.

d.

4-Chloro-5-iodo-7-(2-hydroxyethoxymethyl)pyrrolo [2,3-d]pyrimidine (9b)

Iodine monochloride (0.38 mL) was added dropwise with stirring under a nitrogen atmosphere to a solution of 4-chloro-7-(2-acetoxyethoxymethyl)pyrrolo[2,3-d] pyrimidine (3, 0.82 g) in dry $CH_2Cl_2$ (25 mL). The reaction mixture was stirred at room temperature for 20 hours. The solvent was evaporated at 40° C. under high pressure and the dark purple syrup was placed on the top of a silica gel column. Elution of the column (15×2 cm) with $CHCl_3$ yielded a dark colored syrup, after evaporation of the appropriate UV absorbing fractions, which on trituration with dry ether gave a crystalline product (0.3 g) as colorless needles. These needles were covered with methanol saturated with ammonia (30 mL) at 0° C., and the reaction mixture stirred at room temperature in a pressure bottle for 20 hours.

The solvent was evaporated under high vacuum and the resulting solid was recrystallized from methanol to furnish colorless needles of 9b, 0.21 g (80.75%), mp 154°–155° C. $^1$H-NMR (DMSO-$d_6$): δ8.69 (s, 1, C2-H), 8.14 (s, 1, C6-H), 5.66 (s, 2, N7—$CH_2$), 4.57 (t, 1, exchangeable with $D_2O$, OH), 3.46–3.33 (m, 4, $CH_2$): UV$\lambda_{max}$nm ($\epsilon\times10^4$): (pH 7) 225 (1.8), 296 (0.9); (pH 1) 233 (2.1), 280 (0.95); (pH 11) 228 (0.8), 280 (0.85). Anal. Calcd. for $C_9H_9N_3O_2Cl$: C, 30.55; H, 2.54; N, 11.88. Found: C, 30.87; H. 3.00, N, 11.94.

e.

4-Amino-5-chloro-7-(2-hydroxyethoxymethyl) pyrrolo[2,3-d]-pyrimidine (10)

4,5-Dichloro-7-(2-hydroxyethoxymethyl)pyrrolo[2,3-d]-pyrimidine (7b, 0.07 g) was covered with methanolic-ammonia (20 L) and heated in a sealed reaction vessel at 135° C. for 10 hours. The solvent was evaporated in vacuo to give a thick syrup. This syrup was subjected to column chromatography and elution of the silica gel column (20×3 cm) with 5% MeOH in $CHCl_3$, which, after evaporation of the appropriate UV absorbing fractions, furnished colorless needles of 10, 0.04 g. (66.6%), mp 149°–150° C. $^1$H-NMR (DMSO-$d_6$): δ8.14 (s, 1, C2—H), 7.56 (s, 1, C6—H), 6.92 (bs, 2, exchangeable with $D_2O$, $NH_2$), 5.49 (s, 1, N7—$CH_2$) 4.64 (bs, 1, exchangeable with $D_2O$, OH), 3.43 (m, 4, $CH_2$): UV$\lambda_{max}$nm ($\epsilon\times10^4$): (pH 7) 214 (2.5), 278 (1.3), (pH 1) 233 (2.8), 280 (1.3); (pH 11) 227 (1.4), 278 (1.3). Anal. Calcd. for $C_9H_{11}N_4O_2Cl\cdot1/4H_2O$: C, 43.73; H. 4.66; N, 22.67. Found: C, 43.87; H. 4.36; N. 22.23.

f.

4Amino-5-bromo-7-(2-hydroxyethoxymethyl) pyrrolo[2,3-d]-pyrimidine (11)

5-Bromo4chloro-7(2-hydroxyethoxymethyl)pyrrolo[2,3-d]pyrimidine (8b, 0.75) was dissolved in dry methanol (10 mL) and methanol saturated with ammonia ( 40 mL) was then added to this solution. The reaction mixture was heated at 125° C. in a sealed reaction vessel for 10 hours The solvent was removed at 40° C. under reduced pressure and the resulting solid was then subjected to column chromatography. Elution of the silica get column (20×3 cm) with 5% MeOH in $CHCl_3$ yielded a solid after evaporation of the appropriate UV absorbing fractions.

This solid was recrystallized from $CHCl_3$ to afford 11, 0.18 g (31.25%), mp 163°–164° C. $^1$H-NMR (DMSO-$d_6$): δ8.13 (s, 1, C2—H), 7.55 (s, 1, C6—H), 6.81 (bs, 2, exchangeable with $D_2O$, $NH_2$), 5.5 (s, 2, N7—$CH_2$), 4.62 (m, 1, exchangeable with $D_2O$, OH), 3.42 (m, 4, $CH_2$): UV$\lambda_{max}$nm ($\epsilon\times10^4$): (pH 7) 211 (1.9), 278 (0.9); (pH 1) 233 (2.0),280 (0.94; (pH 11) 227 (0.9), 278 (0.95). Anal. Calcd. for $C_9H_{11}N_4O_2Br$: C, 37.63; H, 3.83; N. 19.51. Found: C, 37.48; H, 3.93; N, 19.77.

g.

4-Amino-5-iodo-7- (2-hydroxyethoxymethyl)pyrrolo [2,3-d]-pyrimidine (12)

4Chloro-5-iodo-7-(2-hydroxyethoxymethyl)pyrrolo[2,3-d]-pyrimidine (9b, 0.3 g) was covered with methanol saturated with ammonia (25 mL) and the reaction mixture was heated at 130° C. in a sealed vessel for 10 hours. The solvent was concentrated in vacuo to give a semi-solid mass which was recrystallized from methanol to afford 12, 0.20 g (71.4%), mp 169°–170° C. $^1$H NMR (DMSO-$d_6$): δ8.7 (s, 1, C2—H), 8.3 (s, 1, C6—H), 5.7 (s, 2, N7—$CH_2$) 4.6 (t, 1, exchangeable with $D_2O$, OH): UV$\lambda_{max}$nm ($\epsilon\times10^4$): (pH 7) 210 (2.0), 280 (0.9); (pH 1) 230 (1.8), 279 (0.9); (pH 11) 228 (0.9), 278 (0.9). Anal. Calcd. for $C_9H_{11}N_4O_2I$; C, 32.43; H, 3.30; N, 16.81. Found: C, 32.49; H, 3.58; N, 16.70.

h.

4-Amino-5-cyano-7-(2-hydroxyethoxymethyl) pyrrolo[2,3-d]-pyrimidine (17a)

4-Amino-6-bromo-5-cyanopyrrolo[2,3-d]pyrimidine (2-38 g, 10 mmole) was dissolved in dry DMF (40 mL). Sodium hydride (97%; 0.25 g; 10 mmole) was added to this solution at 100° C., under a $N_2$ atmosphere, and the solution was stirred for 30 minutes. 2-Acetoxy ethoxymethylbromide (1.98 g; 10 mmole) was then added to the solution with stirring. The reaction mixture was then heated at 100° C. for 6 hour The solution was concentrated in vacuo, and the residue was partitioned in a mixture of EtOAC:$H_2O$ (3:1; 150 mL). The ethyl acetate layer was decanted and washed with $H_2O$ (2×20 mL), and dried over $Na_2SO_4$. The ethyl acetate was evaporated, the residue was absorbed onto silica gel (8.0 g), and then chromatographed on a column (4×80 cm; prepacked in $CH_2Cl_2$), using silica gel (120 g; 60–200 mesh). Elution of the column with $CH_2Cl_2$:$CH_3OH$ (98:2 V:V) gave the 7-substituted compound along with the $N_1$ isomer as an oil (2.3 g: combined yield 65%); all attempts to separate the N7 from its $N_1$-isomer in preparative scale by chromatography was unsuccessful. A small portion of the crude nucleoside mixture was purified by a column of silica gel. A very slow elution of the column with $CH_2Cl_2$:$CH_3OH$ (98:2) gave the N7 compound: $^1$H NMR (DMSO-$d_6$): δ5.65 (S, 2,$C'_1$—$CH_2$), 7.05 (brs, 2, $C_4$—$NH_2$), 8.30 (S, 1, $C_2$—H).

Further elution of the column furnished the $N_1$ isomer which was crystallized from MeOH. $^1$H NMR (DMSO-$d_6$): δ5.72 (S, 2, $C'_1$- $CH_2$), 8.65 (S, 1,$C_2$—H). A mixture of isomers (1.77 g; 5 mmole) was dissolved in a mixture of abs. EtOH and EtOAC (1:2 v/v; 60 mL). Palladium-carbon (5%; 2.0 g) and basic MgO (1.7 g) was added to this solution and the mixture was hydrogenated at 48 psi for 12 hours. The reaction mixture was filtered through a celite pad. The filtrate was evaporated, absorbed onto silica gel (5.0 g), and chromatographed on a silica gel column (2×60 cm; prepacked in $CH_2Cl_2$) using silica gel (80 g, 60–200 mesh). Elution of the column with $CH_2Cl_2$:$CH_3OH$ (96:4, V:V) gave the desired N7 isomer which was then crystallized from EtOH to afford pure compound (0.6 g; yield 44%); m.p. 138° C.; IR (KBr)γ1740 (C=O), 2220 (CN) $cm^{-1}$; UV$\lambda_{max}$nm (ε): (pH 1), 233 (15370), 272 (11946); (MeOH), 228 (10420), 278 (13650); (pH 11), 230 (9900), 278 (14030); $^1$H NMR (DMSO-$d_6$): δ1.95 (s, 3H, $COCH_3$), 3.70 (m, 2H, $CH_2$), 4.05 (m, 2H, $CH_2$), 5.6 (s, 2, $C'_1$—$CH_2$), 6.95 (brs, 2, $C_4$—$NH_2$), 8.30 (s, 1, $C_6$—H), 8.42 (S, 1, $C_2$—H). Anal. ($C_{12}H_{13}N_5O_3$). (C,H,N).

Further elution of the column with $CH_2Cl_2$:$CH_3OH$ (95:5, V:V) afforded another compound which was crystallized from EtOH to obtain the pure N1 isomer (0.39 g; yield 29%); m.p. 165°–166° C.; IR (KBr)γ2220 (CN), 1740 (C=O) $cm^{-1}$; UV$\lambda_{max}$nm(ε): (pH1), 283 (8151); (MeOH), 227 (13900), 277 (13320); (pH11), 229 (8130), 277 (9630); $^1$H NMR (DMSO-$d_6$): δ1.92 (s, 3H, $COCH_3$), 3.82 (m, 2H, $CH_2$), 4.10 (m, 2H, $CH_2$), 5.80 (S, 2H, $C_1$—$CH_2$), 7.15 (brs, 2H, $C_4$—$NH_2$), 7.85 (s, 1H, H), 8.55 (S, 1H, C—H); Anal. ($C_{12}H_{13}N_5O_3$). (C,H,N).

The pure N7 isomer (0.69 g; 2–5 mmole) was stirred with methanolic ammonia (previously saturated at 0° C. 30 ml) in a pressure bottle at 5° C. for 6 hours. At this point, TLC showed the absence of any starting material. The solution was absorbed onto silica gel (5.0 g) and purified by passing through a column (2×80 cm; pre-packed in $CH_2Cl_2$) of silica gel (80 g; 60–200 mesh). Elution of the column with $CH_2Cl_2$: $CH_3OH$ (95:5, V:V) gave a compound which was crystallized from abs. EtOH to afford pure 17a (0.25 g; yield –43%; m.p. 178° C.; IR (KBr)γ2205 (CN) and 3460 (OH) $cm^{-1}$; UV$\lambda_{max}$nm (ε): (pH 1), 235 (6200)270(6200); (MeOH), 278 (4610); (pH 11), 216 (28800), 277 (4644): $^1$H NMR (DMSO-$d_6$): δ3.47 (m, 4, $CH_2$), 4.65 (t, 1, $D_2O$ exchangeable, OH), 5.57 (s, 2, $C'_1$—$CH_2$), 6.87 (brs, 2, $C_4$—$NH_2$), 8.25 (s, 1, $C_6$—H), 8.34 (s, 1, $C_2$—H). Anal. ($C_{10}H_{11}N_5O_2$). (C,H,N).

i.

4-Amino-7-(2-hydroxyethoxymethyl)pyrrolo[2,3-d] pyrimidine-5-thiocarboxamide (17c)

Methyl 4-amino7-(2-hydroxyethoxymethyl)pyrrolo[2,3-d]-pyrimidine-5-formimidate was prepared by first dissolving compound (17a) (0.5 g; 2.15 mmole) in dry MeOH (15 ML). A sodium methoxide (1 M) solution (5 mL) was added and the mixture was stirred at room temperature for 3 hours. This solution was adjusted to pH7 by adding small portions of Dowex 50 (H+ form, prewashed with dry $CH_3OH$). The solution was then quickly filtered to remove the ion-exchange resin followed by concentration of the filtrate in vacuo to a semisolid mass. The residue was purified by a column (2×60 cm; prepacked in CH2$Cl_2$) of silica gel (15 g; 60–200 mesh). Elution of the column with $CH_2Cl_2$:$CH_3OH$ (96:4, V:V) afforded the desired nucleoside which was crystallized from dry $CH_3OH$-$ET_2O$ to afford the pure imidate (0.13 g; yield 23%); mp. 124° C.; IR (KBr)γ3350 (OH) and 1600 $cm^{-1}$; UV$\lambda_{max}$nm:(pH 1), 237 (14700) 280 (12710); (MeOH), 278 (15770); (pH 11), 217 (26100) 278 (13880). $^1$H NMR (DMSO-$d_6$): δ3.50 (nm, 4, $CH_2$), 3.75 (s, 3, $OCH_3$), 5.58 (s, 2, $C_1$"$CH_2$), 7.25 (brs 1, $NH_2$), 7.75 (s, 1, $C_6$—H), 8.06 (s, 1, $C_2$—H), 8.20 (brs, 1, C=NH, 9.98 (brs,1,$NH_2$). Anal. ($C_{11}H_{15}N_5O_3$) C,H,N.

Dry $H_2S$ was passed, with magnetic stirring, for 10 minutes through a sodium methoxide (1 M) solution (12 mL). The methyl imidate (0.26 g; 1 mmole) was then added, in one portion, to this stirred solution of sodium hydrogen sulfide (generated in situ by the action of $H_2S$ and sodium methoxide). The mixture was stirred at room temperature for 4 hours and then allowed to stand at 0° C. for an additional 12 hours The mixture was filtered and the filtrate concentrated in vacuo to a solid mass. The residue was purified by a column (2×60 cm; prepacked in $CH_2Cl_2$) of silica gel (25 g; 60–200 mesh). Elution of the column with $CH_2Cl_2$:$CH_3OH$ (96:4 V:V) gave a compound which was crystallized from $H_2O$ to obtain pure 17c (0.05 g, yield 20%); m p. 186°–188° C.; IR (KBr)γ3380 (OH) and 1620 $cm^{-1}$; UV$\lambda_{max}$nm: (pH 1) 240 (7400) 289 (5600); (MeOH), 284 (5095); (pH 11) 215 (26400)280 (5730); $^1$H NMR (DMSO-$d_6$): δ3.50 (m, 4, $CH_2$), 5.75 (s, 2, $C_1$—$CH_2$), 7.95 (s, 1H, $C_6$—H), 8.02 (brs, 2, $D_2O$-exchangeable, $NH_2$), 8.20 (s, 1, $C_2$—H), 9.60 and 9.75 (brs, 1 each, $D_2O$-exchangeable, $CSNH_2$); Anal. ($C_{10}H_{13}N_5O_2S$). (C,H,N).

j.

4-Amino-5-cyano-7-[(1,3-dihydroxy-2-propoxy) methyl]pyrrolo[2,3-d]pyrimidine (18a)

4-Amino-5-cyano-7-1(1,3-dibenzyloxy-2-propoxy) methyl]-pyrrolo[2,3-d]pyrimidine (1.2 g, 2.71 mmole) was dissolved in dry $CH_2Cl_2$ (70 mL) and cooled to –78° C. using a dry ice-acetone bath. A solution of 1 M $BCl_3$/$CH_2Cl_2$ (20 mL) was then added through a dropping funnel to the cooled solution under a $N_2$ atmosphere. After the addition was completed, the reaction mixture was stirred at –78° C. under a $N_2$ atmosphere for 2 hours and then at –60° C. for 4 more hours. TLC (solvent system, 10% MeOH in $CH_2Cl_2$) showed a complete conversion of the stating material into one product. Cold MeOH (10 mL) was added to the solution at –60° C., and the pH of the solution was immediately adjusted to 7 with 14% $NH_4OH$ solution. The reaction mixture was then brought to room temperature and stirred for I hour. The solvent was evaporated at 40° C. under reduced pressure to give a thick mass which was rotary evaporated with silica gel (2.0 g), and then applied to the top of a column (2×40 cm) packed with wet silica gel using $CH_2Cl_2$ as an eluent.

Elution of the column with $CH_2Cl_2$:$CH_3OH$ (95:5) and evaporation of the desired U.V. absorbing fractions afforded the mono benzyl compound which was crystallized from MeOH to afford pure mono benzyl compound (0.66 g, yield 7%); m.p. 133°–134° C.; IR (KBr)γ3440 (OH), 2220 (CN) $cm^{-1}$; UV$\lambda_{max}$nm: pH 1, 234 (8120), 275 (6590); MeOH, 278 (6660); pH 11,216 (26000), 278 nm (8260); $^1$H NMR (DMSO-$d_6$): δ3.3–3.45 (m, 4H, H-3', H-5'), 3.85 (m, 1H, H-4'), 4.38 (s, 2H, $CH_2$), 4.75 (t, 1H, OH), 5.70 (s, 2H, H-1'), 6.88 (brs, 2H, $NH_2$), 7.18–7.35 (m, 5H, $C_6H_5$), 8.22 (s, 1H, $C_6$—H), 8.32 (s, 1H, $C_2$—H). Anal. ($C_{18}H_{19}N_5O_3$). (C,H, N).

Further elution of the column with $CH_2Cl_2$:$CH_3OH$ (93:7) afforded 4-amino-5-cyano-7-[(1,3-dihydroxy-2-propoxy)methyl]-pyrrolo[2,3-d]pyrimidine (18a), which was crystallized from MeOH to afford analytically pure 18a (0.42 g; yield 59%); m.p. 195° C.; IR (KBr)γ2230 (CN), 3330 and 3440 ($NH_2$ and OH) $cm^{-1}$; UV$\lambda_{max}$nm: (pH 1) 1232 (5000) 273 (3780); MeOH, 278 (5074); pH 11, 216 (27600) 277 (6430); $^1$H NMR (DMSO-$d_6$): δ3.33–3.40 (m, 4H, H-3', H-5'), 3.60 (m, 1H, H4'), 4.63 (t, 2H, $D_2O$ exchangeable, OH), 5.68 (s, 2H, H-1'), 6.87 (brs, 2H, $D_2O$ exchangeable, $NH_2$), 8.25 (s, 1H, $C_6$—H), 8.32 (s, 1H, $C_2$—H). Anal. ($C_{11}H_{13}N_5O_3$). (C,H,N).

k.

4-Amino-7-[(1,3-dihydroxy-2-propoxy)methyl] pyrrolo[2,3-d]-pyrimidine-5-thiocarboxamide (18c)

Dry $H_2S$ was passed through a $NaOCH_3$ solution (1 M) (6 mL) with magnetic stirring and cooling at 0° C. for 10 minutes. Compound 18a (0.13 g; 0.5 mmole) was then added in one portion to the stirred solution of NaSH which had been generated in situ as described above. The mixture was stirred at room temperature for 4 hours and then allowed to stand at 0° C. for an additional 12 hours. The mixture was filtered and the filtrate conc. in vacuo. The residue was purified by a column (2×40 cm; prepacked in $CH_2Cl_2$) of silica gel (20 g; 70–230 mesh). Elution of the column with $CH_2Cl_2$:$CH_3OH$ (94:6) gave the title compound, which was crystallized from $H_2O$ to afford pure 10 (0.04 g; yield 28%); m p. 180°–181° C.; IR (KBr) γ3400 and 3180 ($NH_2$, OH), 1640 $cm^{-1}$; UV$\lambda_{max}$nm: (pH 1), 241 (2750) 301 (1220), MeOH, 283 (5387), pH 11, 216 (26200) 278 (5806); $^1H$ NMR (DMSO-$d_6$): δ3.3–3.45 (m, 4H, H-3', H-4'), 3.60 (m, 1H, H-4'), 4.62 (t, 2H, OH), 5.65 (s, 2H, H-1'), 7.9 (s, 1H, $C_6$—H), 7.98 (brs, 2H, $D_2O$ exchangeable, $NH_2$), 8.15 (s, 1H, $C_2$—H), 9.45 and 9.60 (brs, 1 each, $D_2O$ exchangeable, $CSNH_2$). Anal. ($C_{11}H_{15}N_5O_3S{\cdot}H_2O$). (C,H,N).

1. Synthesis of Precursor Compounds for DHPG Analog Compounds 22 as and 23 a-d

In a typical reaction, 25 mmol of4-chloropyrrolo[2,3-d]-pyrimidine (1) was dissolved in dry DMF (40 mL) and NaH (1.5 eq, 1.5 g, 60% oil dispersion) was added. This solution was stirred until no further $H_2$ evolution was detected (20 min) and 1,3-dibenzyloxypropoxymethyl chloride (1.3 eq, 10.4 g) was added dropwise. After complete addition, the solution was stirred for an additional 40 minutes and water (75 mL) was added. The pH was then neutralized with glacial acetic acid. The aqueous solution was then extracted with EtOAc (1×100 mL, 2×50 mL) and the EtOAc enacts were combined and washed with water (3×50 mL). The EtOAc extracts were then dried over $MgSO_4$ (anhydrous), filtered, and reduced in vacuo at 40° C. to yield a yellow oil. This oil was used without further purification for debenzylation.

This oil (24.38 g, 0.056 mmol) was added to a 1-L flask containing dry $CH_2Cl_2$ (550 mL) and cooled to −78° C. under in argon atmosphere. $BCl_3$ (1M, 210 mL) was then added dropwise maintaining the temperature below −70° C. (internal). Upon complete addition, the solution was stirred for 15 minutes and MeOH (300 mL, 0° C.) was added and the cold solution was neutralized immediately with conc. $NH_4OH$. The solution was then allowed to reach room temperature during which time a white precipitate formed. The white solid was filtered, the solid was discarded, and the filtrate was reduced to a yellow oil. The oil was then suspended in $Et_2O$ and MeOH was carefully added until the oil dissolved and a off-white solid formed. This suspension was then refrigerated for 12 hours after which time the solid was filtered to yield=5.60 g (39%) of 4-chloro-7-[(1,3-dihydroxypropoxy)methyl]pyrrolo[2,3-d]pyrimidine. mp=113.5°–114° C. $^1H$ NMR (DMSO-$d_6$): δ3.18–3.56 (m, 5); 4.67 (t, 2, exchanges with $D_2O$, OH); 5.73 (s, 2, C-1'); 6.68 (d, 1, C-5); 7.89 (d, 1, C-6); 8.67 (s, 1, C-2). Anal. for $C_{10}H_{12}N_3O_3Cl$. (C,H,N).

4,5-Dichloro-7-[(1,3-dihydroxypropoxy)methyl]pyrrolo [2,3-d]pyrimidine was prepared from 4,5-dichloropyrrolo[2, 3-d]pyrimidine to yield 2.72 g (34%). mp=142.5°–143° C. $^1H$ NMR (DMSO-$d_6$): 83.41–3.74 (m, 5); 3.77 (t, 2 exchanges with $D_2O$, OH); 4.93 (s, 2, C-1'); 7.29 (s, 1, C-6); 7.91 (s, 1, C-2). Anal. for $C_{10}H_{11}N_3O_3Cl_2$. (C,H,N).

5-Bromo-4chloro-7-[(1,3-dihydroxypropoxy)methyl] pyrrolo[2,3-d]pyrimidine was prepared from 5-bromo-4-chloropyrrolo[2,3-d]pyrimidine to yield 2.42 g (41%). mp=152°–152.5° C. $^1H$ NMR (DMSO-$d_6$): δ3.23–3.54 (m, 5); 4.08 (t, 2, exchanges with $D_2O$, OH); 5.74 (s, 2, C-1'); 8.12 (s, 1, C-6); 8.70 (s, 1, C-2). Anal. for $C_{10}H_{11}N_3O_3BrCl$. (C,H,N).

4-Chloro-5-iodo-7-[(1,3-dihydroxypropoxy)methyl] pyrrolo[2,3-d]pyrimidine was prepared from 4-chloro-5-iodopyrrolo[2,3-d]-pyrimidine to yield 3.67 g (38%). mp=155°–156° C. $^1H$ NMR (DMSO-$d_6$): δ3.16–3.55 (m, 5), 4.57 (t, 2, exchanges with $D_2O$, OH); 5.72 (s, 2, C-1'), 8.10 (s; 1, C-6), 8.67 (s, 1, C-2). Anal. for $C_{10}H_{11}N_3O_3ClI$. (C,H,N).

m.

4-Amino-5-chloro-7-[(1,3-dihydroxypropoxy) methyl]pyrrolo[2,3-d]pyrimidine (22a)

Compound 22a was prepared by heating the 4,5-dichloro-7-[(1,3-dihydroxypropoxy)methyl]pyrrolo[2,3-d] pyrimidine with saturated methanolic ammonia (15 mL) in a steel reaction vessel. The vessel was then heated to 135° C. for eight hours after which time the vessel was cooled and the solvent was removed in vacuo at 40° C. The resulting solid was then recrystallized from methanol to yield 0.28 g (61%). mp=175°–176.5° C. $^1H$ NMR (DMSO-$d_6$): δ3.22–3.50 (m, 5), 4.58 (t, 2, exchanges with $D_2O$, OH); 5.57 (s, 2, C-1'); 6.88 (bs, 2, exchanges with $D_2O$, $NH_2$) 7.47 (s, 1, C6), 8.11 (s, 1, C-2). Anal. for $C_{10}H_{13}N_4O_3Cl$. (C,H,N).

n.

4-Amino-5-bromo-7-[(1,3-dihydroxypropoxy) methyl]pyrrolo[2,3-d]pyrimidine (22b)

Compound 22b was prepared from 5-bromo4-chloro-7-[ (1,3-dihydroxypropoxy)methyl]pyrrolo[2,3-d]pyrimidine by the method described for 22a to yield 0.27 g (20%). mp=170°–172° C. $^1H$ NMR (DMSO-$d_6$): δ3.15–3.50 (m, 5); 4.59 (t, 2, exchanges with $D_2O$, OH); 5.57 (s, 2, C-1'), 6.80 (bs, 2, exchanges with $D_2O$, $NH_2$); 7.53 (s, 1, C-6); 8.11 (s, 1, C-2). Anal. Calcd. for $C_{10}H_{13}N_4O_3Br$. (C,H,N).

o.

4-Amino-5-iodo-7-[(1,3-dihydroxypropoxy)methyl] pyrrolo[2,3-d]-pyrimidine (22c)

Compound 22c was prepared from 4-chloro-5-iodo-7-[(1, 3-dihydroxypropoxy)methyl]pyrrolo[2,3-d]pyrimidine by the method described for 22a to yield 0.20 g (51%). mp=177°–177.5° C. $^1H$ NMR (DMSO-$d_6$): δ3.22–3.52 (m, 5); 4.58 (t, 2, exchanges with $D_2O$, OH); 5.57 (s, 2, C-1'); 6.66 (bs, 2, exchanges with $D_2O$, $NH_2$); 7.55 (s, 1, C-6); 8.11 (s, 1, C-2). Anal. for $C_{10}H_{13}N_4O_3I$. (C,H,N).

p.

5-Bromo-4-hydroxylamino-7-[(1,3-dihydroxy-propoxy)methyl]-pyrrolo[2,3-d]pyrimidine (23b)

Compound 23b was prepared by dissolving 5-bromo-4-chloro7](1,3-dihydroxypropoxy)methyl]pyrrolo[2,3-d] pyrimidine in iso-propanol (35 mL) and hydroxylamine (50% in $H_2O$, 1 mL). This solution was heated at reflux until no starting material was detected by TLC (2 hours). The solvent was then removed in vacuo to yield a clear, colorless oil that was crystallized from MeOH to yield 0.42 g (61%), mp=180°–181° C. (dec). $^1H$ NMR (DMSO-$d_6$): δ3.23–3.49 (m, 5); 4.56 (t, 2, exchanges with $D_2O$, OH); 5.43 (s, 2, C-1'); 7.16 (s, 1, C-6); 7.45 (d, 1, C-2); 9.70 (s, 1, exchanges with $D_2O$, N-OH); 10.84 (d, 1, exchanges with $D_2O$, NH). Anal. for $C_{10}H_{14}N_4O_4Br$. (C,H,N).

q.

5-Bromo-7-[1,3-dihydroxypropoxy)methyl]pyrrolo [2,3-d]pyrimidine-4 one (23a)

Compound 23a was prepared from 5-bromo-4-chloro7 [(1,3-dihydroxypropoxy)methyl]pyrrolo[2,3-d]pyrimidine by treatment under basic conditions. Anal. for $C_{10}H_{12}N_3O_4$. (C,H,N).

r.

4-Hydroxylamino-5-chloro-7-[(1,3-dihydroxypropoxy)methyl pyrrolo[2,3-d]pyrimidine (23-c)

Compound 23c was prepared from 4-chloro-5-chloro-7-[(1,3-dihydroxypropoxy)methyl]pyrrolo[2,3-d]pyrimidine using the same procedure as described above for the preparation of 23b.

s.

4-Hydroxylamino-5-iodo-7-[(1,3-dihydroxypropoxy) methyl]pyrrolo[2,3-d]pyrimidine (23d)

Compound 23d was prepared in the same manner as 23b and 23c as described above.

D. EXAMPLES OF TESTING AND USE OF COMPOUNDS

The following test methods were followed in generating the data in Tables 1, 2 and 3 and FIGS. 1, 2 and 3:

1. In Vitro Testing in Cell Culture a. Methods

(1) Propagation of Cells and Viruses (a) Cells

The routine growth and passage of KB cells—a human epidermoid neoplastic cell line—was performed in monolayer cultures using minimal essential medium (MEM) with either Hanks salts [MEM(H)] or Earle Salts [MEM(E)] supplemented with 10% calf serum or 5 to 10% fetal bovine serum. The sodium bicarbonate concentration was varied to meet the buffering capacity required. BSC-1 (African green monkey kidney) cells were grown and passaged in Dulbecco modified MEM(E) supplemented with 5% tryptose phosphate broth and 5% horse serum, Cultures of human foreskin fibroblasts (HFF) were grown in medium consisting of MEM(H) with 10% fetal bovine serum.

Cells were passaged at 1:2 to 1:10 dilutions according to conventional procedures by using 0.05% tryspin plus 0.02% EDTA in a HEPES buffered salt solution. HFF cells were passaged only at 1:2 dilutions.

(b) Viruses

The 148 strain of HSV-1 was used in most experiments and was provided by Dr. T. W. Schafer of Schering Corporation. The HF strain of HSV-1 was used in selected experiments and was obtained from Dr. G. H. Cohen, University of Pennsylvania. The Towne strain, plaque-purified isolate $P_o$, of HCMV was a gift of Dr. Mark Stinski, University of Iowa.

High titer HSV-1 stocks have been prepared as follows: Nearly confluent monolayer cultures of KB cells were grown in 32 oz. glass bottles containing MEM(E) buffered with 25 mM HEPES and supplemented with 5% fetal bovine serum and 0.127 gm/liter L-arginine (VGM, virus growth medium). The cultures were infected at a low input multiplicity to reduce the formation of defective virus. After cell cytopathology reached "three to four plus", the cells were harvested by vigorous shaking, and concentrated by centrifugation (800×g for 5 min). The cell pellet was resuspended in 1/40 of the original volume of medium and disrupted by three cycles of freezing and thawing. The resulting virus pools were stored at −76° C. until retrieved for use in experiments.

Stock HCMV was prepared by infecting HFF cells at a multiplicity of infection (m.o.i.) of less than 0.01 plaque-forming units (p.f.u.) per cell. Cell growth medium was changed every four days until cytopathology was evident in all cells (approximately 21 days). Supernatant fluids were retained as the virus stock. Four days later, the remaining cells were disrupted by three cycles of freeze-thawing and the cell plus medium held as an additional source of virus. Storage was in liquid nitrogen.

HSV-1 was titered using monolayer cultures of BSC-1 cells. Cells were planted at $3\times10^5$ cells/well using 6-well cluster dishes. MEM(E) supplemented with 10% fetal bovine serum was employed as medium. After 22–24 hours, cells were 90% confluent and were inoculated in triplicate using at least three ten-fold dilutions with 0.2 ml of the virus suspension to be assayed and incubated in a humidified 4% $CO_2$-90% air atmosphere for one hour to permit viral adsorption. Following virus adsorption, the cell sheet was overlayed with 5 ml of MEM(E) with 5% serum plus 0.5% methocel (4000 CPS) and incubated an additional two to three days. Cells were fixed and stained with 0.1% crystal violet in 20% methanol and macroscopic plaques enumerated.

HCMV was titered in 24-well cluster dishes which were planted to contain $5\times10^4$ HFF cells/well, grown as described above. When the cells were 70 to 80% confluent, 0.2 ml of the virus suspension was added per wall and adsorbed as described above. At least three ten-fold dilutions of each preparation were used. Following virus adsorption, the cell sheets were overlayed with 0.5% methocel (4000 CPS) in maintenance medium [(MEM) with 1.1 gm/liter $NaHCO_3$, 100 units/ml penicillin G, 100 $\mu$g/ml streptomycin, and 5% fetal bovine serum]. The cultures were incubated in a humidified atmosphere of 4% $CO_2$-96% air. Viral foci were visible 5 to 7 days after infection using at least 10-fold magnification. Cells were fixed and stained by a 10-minute exposure to a 0.1% solution of crystal violet in 20% methanol 7 to 12 days after infection. Microscopic foci were enumerated at 20-fold magnification using a Nikon Profile Projector.

(2) Assays for Antiviral Activity (a) HSV-1

Plaque reduction experiments with HSV-1 were performed using monolayer cultures of BSC-1 cells. The assay was performed exactly as described above except that the 0.2 ml virus suspension contained approximately 100 p.f.u. of HSV-1. Compounds to be tested were dissolved in the overlay medium at concentrations usually ranging from 0.1 to 100 $\mu$M in half-or-one $\text{logarithm}_{10}$ dilutions. Titer reduction assays were performed by planting KB cells in 25 $cm^2$ plastic tissue culture flasks 10 to 24 hours prior to infection. At the onset of experiments, logarithmically growing replicate monolayer cultures were 60 to 80% confluent and contained 2.5 to $4.5\times10^6$ cells/flask. Medium was decanted and the cultures were infected with 2 to 10 p.f.u. of HSV-1 per cell. Virus was contained in 1.0 ml of VGM supplemented with 5% fetal bovine serum. After a 1 hour adsorption period at 37° C., the cell sheet was rinsed twice with 2 ml of VGM without serum to remove unadsorbed virus and 5 ml of VGM containing drugs at three to five selected concentrations added in duplicate. Following an 18- to 22-hour incubation at 37° C., infected monolayers were treated with EDTA-trypsin to suspend the cells; aliquots were removed, subjected to three cycles of freezing and thawing, and stored at −76° C. for subsequent virus assay. Virus was titered on BSC-1 cells as described above.

Drug effects were calculated as a percentage of the reduction in virus titers in the presence of each drug concentration compared to the titer obtained in the absence of drug. Acylovir was used as a positive control in all experiments.

(b) HCMV

The effect of compounds of the replication of HCMV has been measured using both a plaque (focus) reduction assay and a titer (yield) reduction assay. For the former, HFF cells in 24-well culture dishes were infected with approximately 50 p.f.u. of HCMV per well using the procedures detailed above. Compounds dissolved in growth medium were added in three to six selected concentrations to triplicate wells following virus adsorption. Following incubation at 37° C. for 7 to 10 days, cell sheets were fixed, stained and microscopic foci were enumerated as described above. Drug effects were calculated as a percentage of reduction in number of foci in the presence of each drug concentration compared to the number observed in the absence of drug. DHPG (ganciclovir) was used as a positive control in all experiments.

For titer reduction assays, HFF cells were planted as described above in 24-well cluster dishes or in 25 $cm^2$ flasks. When monolayers were approximately 70% confluent, HCMV was added at a m.o.i. of 0.5 p.f.u. per cell and adsorbed as detailed above. Compounds dissolved in growth medium were added in one or one-half logarithm $_{10}$ dilutions and incubation continued at 37° C. After 7 to 10 days of incubation, culture dishes or flasks were frozen at 76° C. For titer determination, cells were thawed and then subjected to two more cycles of freezing and thawing at 37° C. Serial, one-logarithm$_{10}$ dilutions of the final suspension were prepared and inoculated onto new cultures of HFF cells. Titer determination was as detailed above in part (1) (b).

(3) Cytotoxicity Assays (a) Protocol for Determining Effects of Compounds on DNA, RNA and Protein Synthesis KB or HFF cells were planted using a Costar Transplate-96 (Costar, Cambridge, Mass.) in Costar 96-well cluster dishes at a concentration of 10,000 to 12,000 cells per well. Wells were suspended in 200 $\mu$l of medium [MEM(H) plus 0.7 gm/liter $NaCHO_3$ supplemented with 10% calf serum] per well. After incubation of 16 to 24 hours at 37° C. in a humidified atmosphere of 4% $CO_2$ in air, 150 $\mu$l of medium was removed per well. One-hundred $\mu$l of medium with or without compounds in twice their final concentrations was added to each well using a Titertek Multichannel Pipette. Final concentrations of compounds ranged from 0.1 to 320 $\mu$M. Fifty $\mu$l of medium containing radioactive precursors also was added to each well to give a final concentration to 1 to 3 $\mu$Ci/ml of labeled precursor. [$^3$H] Thd was diluted with unlabeled dThd to give a final concentration of 3 or 6 $\mu$M.

Following addition of drugs and labeled precursors, plates were incubated as described above for an additional 18 to 24 hours. Logarithmic cell growth occurred during this time with continual uptake of labeled precursor At the end of the incubation period, cells were individually harvested from each well using a Skatron Cell harvester (Skatron, Inc., Sterling, Va.). Cultures for individual wells were harvested onto filter paper and washed free of unincorporated label with nine sequential washes with 5% trichloroacetic acid, nine washes with water, and nine with ethanol using the Skatron unit. Filters were dried, circles from individual cultures were punched from the filter mat and placed into mini-vials. Liquid scintillation solution was added, and radioactivity determined in a Beckman model LS8100 liquid scintillation spectrometer. All samples were counted for 2.0 minutes each, with three rounds of counting. Counts per minute were determined following the application of statistical methods to eliminate count rates which fell outside distribution limits defined by Chauvenet's rejection criterion.

All analyses were performed in triplicate. That is, three culture wells were used per time point, radioactive precursor, and drug concentration in all experiments. Results from triplicate assays were converted to percent of control and plotted as log dose-response curves from which 50% inhibitor ($I_{50}$) concentrations were interpolated. Three concentrations of vidarabine were included on all plates as a positive control.

(b) Visual Scoring

Cytotoxicity produced in HFF and BSC-1 cells was estimated by visual scoring of cells not affected by virus infection in the HCMV and HSV-1 plaque reduction assays. Cytopathology was estimated at 35- and 60-fold magnification and scored on a zero to four plus basis. Wells were scored on the day of staining.

(4) Cell Growth Rates

Population doubling times and cell viability were measured in uninfected HFF and/or KB cells. Cells were planted in replicate 6-well plastic tissue culture dishes or in 25 $cm^2$ flasks as described above in part 1. Following an incubation period during which cells attached to the substrate, medium was decanted, the cell sheet rinsed once with HBS, and fresh medium added. The medium consisted of MEM(E) with 1.1 gm $NaHCO_3$/liter and 10% fetal bovine or calf serum plus appropriate log or half-log concentrations of drug. After additional periods of incubation from 1 to 72 hours at 37° C., cells were harvested by means of 0.05% trypsin plus 0.02% EDTA in a HEPES-buffered salt solution. Cells were enumerated using either a Coulter counter or a hemocytometer and viability determining using trypsin blue dye exclusion.

(5) Plating Efficiency

A plating efficiency assay was used to confirm and extend results described above. Briefly, KB cells were suspended in growth medium and an aliquot containing 1000 cells was added to a 140×25 mm petri dish. Growth medium (40 ml) containing selected concentrations of test compounds was added and the cultures incubated in a humidified atmosphere of 4% $CO_2$-96% air, 37° C. for 14 days. Medium then was decanted and colonies fixed with methanol and stained with 0.1% crystal violet in 20% methanol. Macroscopic colonies greater than 1 mm in diameter were enumerated. Drug effects were calculated as a percentage of reduction in number of colonies formed in the presence of each drug concentration compared to the number of colonies formed in the absence of drugs. Dose-response curves were generated and $I_{50}$ concentrations for inhibition of plating/colony formation were calculated.

(6) Viral DNA Determination by "Dot-Blot" Hybridization

The amount of HCMV DNA synthesis was determined in two types of experiments: (a) as an integral part of HCMV titer (yield) reduction experiments and (b) as separate experiments to determine only the amount of viral DNA synthesis in the absence or presence of test compounds.

(a) Determination in Titer Reduction Experiments

HFF cells were planted in 25 $cm^2$ flasks and infected with HCMV as described in part 2 and incubated at 37° C. Before harvesting at selected times by the addition of 0.1 volume of 0.2M EDTA, an aliquot of medium was removed for determination of HCMV titer. After harvesting cells into the medium, aliquots were retained for determination of HCMV DNA by hybridization.

(b) Determination of HCMV DNA in Microtiter Plate Culture

HFF cells were planted in 96-well cluster plates at 20,000 cell/well in 200 $\mu$l of growth medium [MEM(E)] with 1.1 gm/liter $NaHCO_3$ and 10% fetal bovine serum. After incubation in a humidified atmosphere of 4% $CO_2$-96% air for 1 to 2 days, growth medium was aspirated and the 70% confluent cells were infected at a m.o.i. of 0.5 p.f.u. per cell by addition of HCMV in 100 $\mu$l of MEM(E) with 1.1 gm/l liter $NaHCO_3$ and 5% fetal bovine serum (maintenance medium). Following a 1-hour incubation at 37° C. for virus adsorption, 100 $\mu$l of selected concentrations of test compounds were added to each of triplicate wells in twice their final concentration of maintenance medium. Usually 3 to 6 concentrations of compounds were tested in 3.2- or 10-fold dilutions along with appropriate triplicate no drug and no virus controls. Plates were incubated for 7 days and harvested by addition of 100 $\mu$l of 0.25M EDTA per well. After a 30-minute incubation of 37° C. to free the cells, the contents of the wells were filtered as described below or frozen at −76° C. for subsequent analysis. The following procedure adapted from Gadler, H., Antimicrob. Agents Chemother., 24:370 (1983) was employed for the hybridization portion of the assay:

The contents of each well were removed and filtered through Gene Screen TM (NEN Research Products), presoaked in 10×SSC (1×SSC is 0.15M NaCl, 0.015M NaCitrate), using a 96-well filtration manifold (Schleicher and Schuell). The original microtiter plate wells were rinsed with 200 $\mu$l HEPES buffered saline and the contents added to the filter manifold.

The Gene Screen membrane was dried at room temperature and then baked at 80° to 100° C. for 3 to 4 hours. The DNA on the membrane was denatured by placing the membrane (sample side up) sequentially on filter papers soaked in (a) 0.5M NaOH for 30 minutes, (b) 0.1 M NaOH 1.5M NaCl for 5 minutes (c) 1M Tris HCl, pH 7.5 twice each for 5 minutes, (d) 0.5M Tris HCl, pH 7.5, 1.5M NaCl for 5 minutes and then dried at room temperature. The membrane was added to a "hybridization bag" and prehybridized at 65° C. for (greater or equal to) 6 hours in 10 ml 0.2% polyvinylpyrrolidone (MW 40,000); 0.2% ficoll (MW 400,000); 0.2% bovine serum albumin; 0.05 M Tris HCl, pH 7.5; 0.1% sodium pyrophosphate; 1M NaCl; 10% dextran sulfate (ME 500,000) and 0.1 mg/ml denatured salmon testes DNA.

1.1 $\mu$g of radioactively-labeled DNA probe was added to the prehybridization mixture and incubated overnight at 65° C. The probe was plasmid pACYC-184, containing Xba I fragment 1c of HCMV. It was amplified in E. Coli HB101, rec $A^-$ provided through the courtesy of Dr. Mark Stinski, University of Iowa. The probe was nick translated with [$^{32}$P]dCTP using a kit obtained from Cooper Biomedical, denatured, and used directly for hybridization.

Following hybridization, the membrane was washed sequentially in 100 ml 2×SSC at room temperature twice each for 5 minutes, 100 ml 2×SCC plus 1% SDS at 65° C. twice each for 30 minutes and then 100 ml 0.1×SSC at room temperature twice each for 30 minute. The membrane was dried at room temperature and each filtration spot was cut from the membrane and placed into 4 ml of toluene/DPO scintillant and hybridized label counted in a liquid scintillation spectrometer.

(7) Data Analysis

Dose-response relationships were used to compare drug effects. These were constructed by linearly regressing the percent inhibition of parameters derived in the preceding sections against log drug concentrations. The 50% inhibitory ($I_{50}$) concentrations were calculated from the regression lines using the methods described by Goldstein. See Goldstein, A., Biostatistics: An Introductory Text, MacMillan, N.Y., 1964, pp. 156–161. The three $I_{50}$ concentrations for inhibition of DNA, RNA, and protein synthesis were averaged and were reported in the tables. Along with the $I_{50}$ concentration for visual cytotoxicity, the averaged $I_{50}$ concentrations are compared to $I_{50}$ concentrations for inhibition for HCMV or HSV-1 replication. Compounds for which the ratio of cytotoxicity $I_{50}$ concentrations to antiviral $I_{50}$ concentrations (in vitro therapeutic index) were greater than 10, were considered for further study.

b. Results in Cell Culture (1) Antiviral Activity and Cytotoxicity of 7-[(hydroxyethoxy) methyl]-pyrrolo[2,3-d]pyrimidines (HEM nucleosides)

The 4-amino-5-Cl-, 5-Br-, 5-I, and 5-thioamide-7-[(2-hydroxyethoxy)methyl]pyrrolo[2,3-d]pyrimidines (compounds UMJD No.[b] 100, 102, 104, 229, respectively, also shown in the Tables as compounds No.[a] 10, 11, 12 17c but hereinafter referred to by their UMJD No.[b]) were active against HCMV. This activity was quite surprising because the related compound, acyclovir, had only modest activity against HCMV (Tables 1 and 2). Similar but less potent activity also was found for compounds 100, 102, and 104 against herpes simplex virus type 1 (HSV-1) (Table 1).

All compounds produced only little visual cytotoxicity in HFF cells and affected [$^3$H]Urd and $^3$H-amino acid incorporation in KB cells only at concentrations over 100 $\mu$M. All three 4-amino compounds were potent inhibitors of [$^3$H] dThd incorporation ($I_{50}$ less than 1 $\mu$M). The latter may be misleading, however, because when DNA was labeled with inorganic phosphate, the $I_{50}$ was approximately 10 $\mu$M. A similar circumstance exists with ribavirin where [$^3$H]dThd incorporation seriously overestimates inhibition of cellular DNA synthesis. See Drach, J. C. et al., Science, 212:549 (1981). When labeled precursor experiments were repeated in HFF cells, the Cl- and Br-compounds inhibited [$^{32}$P] phosphate labeling of DNA by only 10% at 100 $\mu$M. Because of these interesting observations, secondary tests were performed.

FIG. 1 and Table 1 illustrate the effects of the halogen compounds on HCMV in titer reduction assays. The compounds required 32 to 100 $\mu$M concentrations to give a 2–3 log reduction in virus titer. These results for compounds UMJD 102 and 1–4 were approximately 10-fold better than for acyclovir (FIG. 1).

In more extensive cytotoxicity testing, the halogenated compounds were tested for effects on the growth of KB cells. Populations doubling times were calculated from the logarithmic portions of growth curves and were as follows:

| Drug Concentration (μM) | Population Doubling time (hr) in the Presence of UMJD 100 (5-Cl) | UMJD 102 (5-Br) | UMJD 104 (5-I) |
|---|---|---|---|
| 0.0 | 23 | 23 | 23 |
| 0.1 | ND | 30 | 26 |
| 1.0 | 25 | 43 | 25 |
| 10.0 | 25 | 84 | 30 |
| 100.0 | 27 | ND | ND |

As seen from the chart above, the 5-Cl compound affected KB cell growth to only a minor extent even at a concentration of 100 μM. The effect of these compounds on the growth of human diploid fibroblasts (HFF cells) was less pronounced. During a 70-hour incubation, control cells underwent two doublings. In the presence of 10 or 32 μM of compound UMJD 100 there was no decrease in the number of cells present at 70 hours. A 100 μM concentration reduced the number of cells by less than 10%. The effects of the Br and I compounds UMJD 102, UMJD 104, respectively, were more pronounced. Nonetheless, cells still underwent one population doubling in 70 hours in the presence of 100 μM concentrations of either compound. Compound UMJD 100 also did not affect DNA synthesis in human PBLs stimulated by pokeweed mitogen or concanavalin A at concentrations of 0.1, 1, 10 and 100 μM.

synthesis occurred at levels slightly lower than those required for inhibition of virus replication (Table 2), suggesting that the compounds may act by inhibiting viral DNA synthesis.

(2) Antiviral Activity and Cytotoxicity of 7-[(Dihydroxypropoxy)methyl]-pyrrolo[2,3-d]-pyrimidines, (DHPM nucleosides)

Results with the analogs in the DHPM series were more dramatic. Table 1 illustrates that the 4-amino-5-Cl, 5-Br, 5-I and 5-$CSNH_2$ analogs as well as the 4-hydroxylamino-5-Cl, 5-Br, and 5-I analogs were active against HCMV. FIG. 2 shows that the 4-amino-5-Br compound (UMJD 183) was most active and reduced HCMV titers by nearly 5 logs (100,000-fold) at 10 μM. The 5-Cl compound (UMJD 186) and the 5-I compound (UMJD 330) also produced 5-log reduction in virus titer but required a 10-fold higher concentration. FIG. 3 illustrates that the 4-hydroxylamino-5-Cl (UMJD 328), 5-Br (UMJD 299) and 5-I (UMJD 329) analogs were active and nearly as potent as the 4-amino analogs. These compounds reduced virus titer 100 to 100,000-fold at a concentration of 100 μM.

As discussed above, the 5-Br-compound in the HEM series (UMJD 102) was cytostatic. Concentrations as low at 0.1 μM inhibited the growth of KB cells. When similar experiments were performed with the 4-amino-5-Br compound in the DHPM series (UMJD 183), growth of KB cells also was inhibited, but to a lesser extent. Cell growth occurred up to 20 hours in the presence of the drug before slowing or stopping. In separate experiments, growth occurred in the presence of up to 32 μM drug for 50 hours, but at a reduced rate. In contrast, the 4-hydroxylamino-5-Br analog (UMJD 299) and the 4-hydroxyamino-5-I analog (UMJD 329) had considerably lesser effects on cell growth

TABLE 1

Antiviral Activity and Cytotoxicity of 4,5-Substituted 7-Acyclic Pyrrolo[2,3-d]pyrimidines.

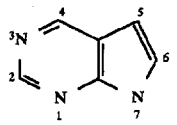

| Compound: UMJD No.[a] | UMJD No.[b] | Substituent 4 | 5 | 7[v] | 50% Inhibitory Concentration (μM): HCMV Plaque | HCMV Yield[p] | HSV-I[r] Plaque | HSV-I[r] Yield[p] | Cytotoxicity HFF[c] | BSC[c] | KB[d] |
|---|---|---|---|---|---|---|---|---|---|---|---|
| *Acyclovir*[e] | | | | HEM | 63 | 90 | 4 | 7 | >100 | >100 | >100 |
| *Ganciclovir (DHPG)*[e] | | | | DHPM | $8.7^{h(54)}$ | 1.8 | 4.5 | 1.2 | $>100^{h(23)}$ | >100 | 1000 |
| 10 | 100 | $NH_2$ | Cl | HEM | $22^{h(5)}$ | $46^{h(3)}$ | 77 | 50 | $>100^{h(5)}$ | >100 | $350^{h(5),t}$ |
| 11 | 102 | $NH_2$ | Br | HEM | $3.5^{h(6)}$ | $13^{h(3)}$ | $11^{h(2)}$ | $30^{h(2)}$ | $100^{h(5)}$ | $>100^{h(2)}$ | $100^{h(5),t}$ |
| 12 | 104 | $NH_2$ | I | HEM | $24^{h(3)}$ | $14^{h(3)}$ | 250 | >100 | $100^{h(2)}$ | >100 | $94^{h(2),t}$ |
| 17c | 229 | $NH_2$ | $CSNH_2$ | HEM | $11^{h(2)}$ | $80^{h(2)}$ | >100 | — | $100^{h(2)}$ | >100 | $>100^{t}$ |
| 22a | 186 | $NH_2$ | Cl | DHPM | $9.8^{h(2)}$ | $8^{h(2)}$ | 16 | 12 3.5 | $>100^{h(2)}$ | >100 | $>100^{t}$ |
| 22b | 183 | $NH_2$ | Br | DHPM | $1.6^{h(5)}$ | $1.9^{h(2)}$ | 2 | 17 | $>100^{h(2)}$ | $>100^{h(2)}$ | 25 |
| 22c | 330 | $NH_2$ | I | DHPM | $3.1^{h(3)}$ | 0.9 | — | — | $>100^{h(3)}$ | — | — |
| 18c | 239 | $NH_2$ | $CSNH_2$ | DHPM | $8.0^{h(2)}$ | 25 | >100 | — | $>100^{h(2)}$ | >100 | $>100^{h(2),t}$ |
| 23c | 328 | NHOH | Cl | DHPM | $56^{h(2)}$ | 24 | — | — | $>100^{h(3)}$ | — | — |
| 23b | 299 | NHOH | Br | DHPM | $1.2^{h(3)}$ | 10 | 2.9 | >100 | $>100^{h(3)}$ | — | 357 |
| 23d | 329 | NHOH | I | DHPM | $18^{h(3)}$ | 3.2 | — | — | $>100^{h(3)}$ | — | — |

Additional tests utilizing flow cytometry indicated that these compounds were cytostatic, not cytotoxic.

The effects of the three halogen compounds on HCMV DNA synthesis were also measured. Inhibition of viral DNA KB cells grew at nearly control rates in the presence of 10 μM compound UMJD 299 and UMJD 329. A concentration of 100 μM reduced growth rate by >50%.

TABLE 2

Antiviral Activity and Inhibition of Viral DNA Synthesis 4,5-Subtituted 7-Acyclic Pyrrolo[2,3-d]pyrimidines.

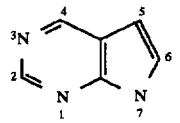

| Compound | | | | | | 50% Inhibitory Concentration (μM) | |
|---|---|---|---|---|---|---|---|
| | UMJD | | Substituent | | | HCMV Titer, Plaque or Yield Reduction | HCMV DNA Synthesis |
| Name | No.[a] | No.[b] | 4 | 5 | 7[v] | | |
| *Acyclovir*[e] | | | | | HEM | 63 | 35 |
| *(DHPG)*[e] | | | | | DHPM | 8.8[h(23)] | 1.2[h(4)] |
| Compound 100 | 112 | 100 | $H_2N$ | Cl | HEM | 16[h(4)] | 15[h(3)] |
| Compound 102 | 111 | 102 | $H_2N$ | Br | HEM | 3.9[f,h(3)] | 3.2[h(3)] |
| Compound 104 | 113 | 104 | $H_2N$ | I | HEM | 24[h(3)] | 47[h(2)] |

FOOTNOTES TO TABLE 1–2

[a]Number for chemcial structure present in text.

[b]Identification number assigned to compounds provided to Drach from Townsend.

[c]Visual cytotoxicity scored on HFF or BSC-1 cells at time of HCMV or HSV-1 plaque enumerations.

[d]Average percent inhibition of DNA, RNA and protein synthesis determined in KB cells as described in the text.

[e]Known antiviral drugs. Acyclovir is marketed under the brand name "Zovirar".

[h]Average $I_{50}$ concentration derived from (. . .) experiments.

[p]90% inhibitory concentrations ($I_{90}$) presented

[r]Results with HSV-1 strain S-18. $I_{50}$ with HF strain = 36, >100, 28 54 μM for acyclovir, compounds 100, 102 and 104 respectively.

[t]Effect on [$^3$H]Urd and $^3$H-amino acid incorporation only. The following effects were observed on [$^3$H]dThd incorporation:

| Compound | $I_{50}$ |
|---|---|
| 100 | 0.82 |
| 102 | 0.13 |
| 104 | 1.2 |
| 186 | 28 |
| 229 | 10 |
| 239 | 28 |

[v]Abbreviations used are DHPM-(dihydroxypropoxy)methyl; HEM:(hydroxyethoxy)methyl.

2. In Vivo Testing a. Methods

Compound UMJD 183 was tested in mice infected with murine cytomegalovirus (MCMV). This animal model has been recognized as having capabilities predictive of efficacy in humans.

Compound UMJD 183 and the drug ganciclovir (DHPG) were administered to groups of 15 mice each at doses and times of administration shown in Table 3. Each compound at all doses was administered intraperitoneally twice daily for five days beginning at either 6, 24 or 48 hours after virus inoculation. Animals were observed daily and the number dying each day recorded. The mean day of death (MDD) and the percent of survivors were calculated and are presented in Table 3 below.

b. Results in Vivo

Table 3 below presents results from in vivo experiments with compound UMJD 183. Administered alone to uninfected animals, the drug showed virtually no toxicity—1 death in 60 animals, which may not have been drug-related. When administered to animals infected with lethal amounts of murine cytomegalovirus (MCMV), compound UMJD 183 prolonged life span (increased the mean day of death) at all doses. At the optimum dose of 5.6 mg/kg, it produced highly significant increases in the number of animals surviving the virus infection. Even when the compound was administered 48 hours after virus infection, compound UMJD 183 reduced mortality from 80–93% in controls to 40% in the presence of 5.6 mg/kg of the drug. When UMJD 183 was administered sooner, 6 or 24 hours after virus infection, mortality was reduced further to 7 or 20%, respectively.

TABLE 3

Effect of Treatment With UMJD-183 or DHPC on the Mortality of Mice Inculated with MCMV

| | Mortality | | | | |
|---|---|---|---|---|---|
| Treatment[a] | Number | Percent | P-Value | MDD[b] | P-Value |
| Control | 12/15 | 80 | — | 4.6 | — |
| Placebo at 24 h | 14/15 | 93 | NS[c] | 4.4 | NS |
| UMJD-183 | | | | | |
| 50 mg/kg at 6h | 9/15 | 60 | NS | 10.8 | <0.001 |
| 50 mg/kg at 24 h | 14/15 | 93 | NS | 8.8 | <0.001 |

TABLE 3-continued

Effect of Treatment With UMJD-183 or DHPC on the Mortality of Mice Inculated with MCMV

| Treatment[a] | Mortality Number | Mortality Percent | P-Value | MDD[b] | P-Value |
|---|---|---|---|---|---|
| 50 mg/kg at 48 h | 13/15 | 97 | NS | 7.5 | <0.01 |
| 50 mg/kg - Toxicity[d] | 0/15 | 0 | — | — | — |
| 16.7 mg/kg 6 h | 9/15 | 60 | NS | 8.7 | <0.001 |
| 16.7 mg/kg 24 h | 12/15 | 80 | NS | 7.1 | <0.01 |
| 16.7 mg/kg 48 h | 13/15 | 87 | NS | 8.4 | <0.001 |
| 16.7 mg/kg - Toxicity | 1/15 | 7 | — | 5.0 | — |
| 5.6 mg/kg 6 h | 1/15 | 7 | <0.001 | 8.0 | NS |
| 5.6 mg/kg 24 h | 3/15 | 20 | <0.001 | 6.3 | <0.01 |
| 5.6 mg/kg 48 h | 6/15 | 40 | <0.01 | 5.5 | NS |
| 5.6 mg/kg - Toxicity | 0/15 | 0 | — | — | — |
| 1.9 mg/kg 6 h | 5/15 | 33 | 0.001 | 6.2 | <0.01 |
| 1.9 mg/kg 24 h | 9/15 | 60 | NS | 4.8 | NS |
| 1.9 mg/kg 48 h | 10/15 | 67 | NS | 4.8 | NS |
| 1.9 mg/kg - Toxicity | 0/15 | 0 | — | — | — |
| DHPG | | | | | |
| 16.7 mg/kg 6 h | 4/15 | 27 | <0.001 | 3.8 | NS |
| 16.7 mg/kg 24 h | 7/15 | 47 | <0.01 | 5.3 | NS |
| 16.7 mg/kg 48 h | 8/15 | 53 | <0.05 | 5.5 | <0.05 |
| 5.6 mg/kg 6 h | 5/15 | 33 | 0.001 | 4.2 | NS |
| 5.6 mg/kg 24 h | 7/15 | 47 | <0.01 | 5.3 | NS |
| 5.6 mg/kg 48 h | 10/15 | 67 | NS | 5.5 | <0.01 |
| 1.9 mg/kg 6 h | 5/15 | 33 | 0.001 | 5.4 | NS |
| 1.9 mg/kg 24 h | 12/15 | 80 | NS | 4.9 | NS |
| 1.9 mg/kg 48 h | 11/15 | 73 | NS | 4.9 | NS |
| 0.6 mg/kg 6 h | 14/15 | 93 | NS | 4.6 | NS |
| 0.6 mg/kg 24 h | 12/15 | 80 | NS | 5.4 | 0.01 |
| 0.6 mg/kg 48 h | 14/15 | 93 | NS | 5.3 | 0.01 |

[a]Animlas were treated i.p. twice daily for 5 days with the doses stated above. Treatment was initiated at the times indicated following virus inoculations.
[b]MDD = Mean Day of Death.
[c]NS = Not Significant.
[d]Drug toxicity control. No virus administered.

What is claimed is:

1. A compound selected from the group consisting of compounds of the following formula and pharmaceutically acceptable salts thereof:

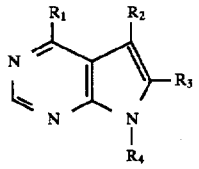

where $R_1$ is [$NH_2$, NHOH,] OH or H;
$R_2$ is $CSNH_2$, Cl, Br, I, F, 2-buten-1-yl, 5-(1-hydroxyethyl) or 5-(1-methoxyethyl);
$R_3$ is H, $NH_2$ or Br; and
$R_4$ is (1,3-dihydroxy-2-propoxy)methyl,
(2-hydroxyethoxy)methyl,
(2-acetoxyethoxy)methyl, 2-hydroxy-1-(1,3-dihydroxy-2-propoxy)ethyl,
(2-phosphonylmethoxy)ethyl or 3-hydroxy-2-phosphonylmethoxypropyl.

[2. The compound of claim 1 wherein $R_1$ is $NH_2$, $R_2$ is Cl, $R_3$ is H and $R_4$ is (2-hydroxyethoxy)methyl.]

[3. The compound of claim 1 wherein $R_1$ is $NH_2$, $R_2$ is Br, $R_3$ is H and $R_4$ is (2-hydroxyethoxy)methyl.]

[4. The compound of claim 1 wherein $R_1$ is $NH_2$, $R_2$ is I, $R_3$ is H and $R_4$ is (2-hydroxyethoxy)methyl.]

[5. The compound of claim 1 wherein $R_1$ is $NH_2$, $R_2$ is thiocarboxamide, $R_3$ is H and $R_4$ is (2-hydroxyethoxy) methyl.]

[6. The compound of claim 1 wherein $R_1$ is $NH_2$, $R_2$ is Cl, $R_3$ is H and $R_4$ is (1,3-dihydroxy-2-propoxy)methyl.]

[7. The compound of claim 1 wherein $R_1$ is $NH_2$, $R_2$ is Br, $R_3$ is H and $R_4$ is (1,3-dihydroxy-2-propoxy)methyl.]

[8. The compound of claim 1 wherein $R_1$ is $NH_2$, $R_2$ is I, $R_3$ is H and $R_4$ is (1,3-dihydroxy-2-propoxy)methyl.]

[9. The compound of claim 1 wherein $R_1$ is $NH_2$, $R_2$ is thiocarboxamide, $R_3$ is H and $R_4$ is (1,3-dihydroxy-2-propoxy)methyl.]

[10. The compound of claim 1 wherein $R_1$ is $NH_2$, $R_2$ is thiocarboxamide, $R_3$ is H and $R_4$ is 2-hydroxy-1-(1,3-dihydroxy-2-propoxy)ethyl.]

11. The compound of claim 1 wherein $R_1$ is OH, $R_2$ is Cl, $R_3$ is H and $R_4$ is (1,3-dihydroxy-2-propoxy)methyl.

[12. The compound of claim 1 wherein $R_1$ is NHOH, $R_2$ is Cl, $R_3$ is H and $R_4$ is (1,3-dihydroxy-2-propoxy)methyl.]

13. The compound of claim 1 wherein $R_1$ is OH, $R_2$ is Br, $R_3$is H and $R_4$ is (1,3-dihydroxy-2-propoxy)methyl.

[14. The compound of claim 1 wherein $R_1$ is NHOH, $R_2$ is Br, $R_3$ is H and $R_4$ is (1,3-dihydroxy-2-propoxy)methyl.]

[15. The compound of claim 1 wherein $R_1$ is NHOH, $R_2$ is I, $R_3$ is H and $R_4$ is (1,3-dihydroxy-2-propoxy)methyl.]

16. The compound of claim 1 wherein $R_1$ is OH, $R_2$ is I, $R_3$ is H and $R_4$ is (1,3-dihydroxy-2-propoxy)methyl.

17. The compound of claim 1 wherein $R_3$ is $NH_2$.

18. The compound of claim 1 wherein $R_3$ is Br.

19. A method of treating mammalian cells infected with a mammalian infectious virus selected from the group consisting of human cytomegalovirus and herpes simplex virus, the method comprising the step of contacting said cells with a composition comprising a therapeutically effective amount of a compound selected from the group consisting of compounds of the following formula or a pharmaceutically acceptable salt thereof:

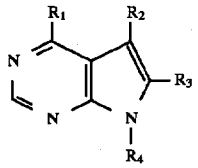

where $R_1$ is [$NH_2$, NHOH,] OH or H;
$R_2$ is $CSNH_2$, Cl, Br, I, F, 2-buten-1-yl, 5-(1-hydroxyethyl) or 5-(1-methoxyethyl);
$R_3$ is H, $NH_2$ or Br; and
$R_4$ is (1,3-dihydroxy-2-propoxy)methyl,
(2-hydroxyethoxy)methyl,
(2-acetoxyethoxy)methyl, 2-hydroxy-1-(1,3-dihydroxy-2-propoxy)ethyl,
(2-phosphonylmethoxy)ethyl or 3-hydroxy-2-phosphonylmethoxypropyl,
wherein said contacting of said cells comprises in vivo administration of said composition to the infected mammal.

20. The method of claim 19 wherein said contacting of said cells comprises in vivo administration of said composition to a mammal.

21. The method of claim 19 wherein said cells are human cells.

22. The method of claim 20 wherein said mammal is a human.

23. The method of claim 19 wherein the virus is human cytomegalovirus.

24. The method of claim 19 wherein the virus is herpes simplex virus type 1.

[25. The method of claim 19 wherein $R_1$ is $NH_2$, $R_2$ is a halogen group, $R_3$ is H and $R_4$ is (1,3-dihydroxy-2-propoxy) methyl.]

[26. The method of claim 19 wherein $R_1$ is NHOH, $R_2$ is a halogen group, $R_3$ is H and $R_4$ is (1,3-dihydroxy-2-propoxy)methyl.]

[27. The method of claim 19 wherein $R_1$ is $NH_2$, $R_2$ is a halogen group, $R_3$ is H and $R_4$ is (2-hydroxyethoxy)methyl.]

[28. The method of claim 25 wherein $R_2$ is Cl.]

[29. The method of claim 25 wherein $R_2$ is Br.]

[30. The method of claim 25 wherein $R_2$ is I.]

[31. The method of claim 26 wherein $R_2$ is Cl.]

[32. The method of claim 26 wherein $R_2$ is Br.]

[33. The method of claim 26 wherein $R_2$ is I.]

[34. The method of claim 27 wherein $R_2$ is Cl.]

[35. The method of claim 27 wherein $R_2$ is Br.]

[36. The method of claim 27 wherein $R_2$ is I.]

[37. The method of claim 19 wherein $R_1$ is $NH_1$, $R_2$ is $CSNH_2$, $R_3$ is H and $R_4$ is (1,3-dihydroxy-2-propoxy) methyl.]

[38. The method of claim 19 wherein $R_1$ is $NH_2$, $R_2$ is $CSNH_2$, $R_3$ is H and $R_4$ is (2-hydroxyethoxy)methyl.]

39. The method of claim 19 wherein $R_3$ is $NH_2$.

40. The method of claim 19 wherein $R_3$ is Br.

41. A composition comprising a compound selected from the group consisting of compounds of the following formula and pharmaceutically acceptable salts thereof:

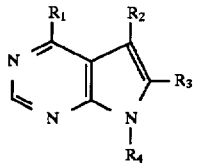

where $R_1$ is [$NH_2$, NHOH,] OH or H;

$R_2$ $CSNH_2$, Cl, Br, I, F, 2-buten-1-yl, 5-(1-hydroxyethyl) or 5-(1-methoxyethyl);

$R_3$ is H, $NH_2$ or Br; and $R_4$ is (1,3-dihydroxy-2-propoxy)methyl, (2-hydroxyethoxy)methyl, (2-acetoxyethoxy)methyl, 2-hydroxy-1-(1,3dihydroxy-2-propoxy)ethyl, (2-phosphonylmethoxy)ethyl or 3-hydroxy-2-phosphonylmethoxypropyl;

and a pharmaceutically acceptable carrier.

* * * * *